(12) United States Patent
Soukka et al.

(10) Patent No.: US 7,790,392 B2
(45) Date of Patent: Sep. 7, 2010

(54) HOMOGENEOUS LUMINESCENCE BIOASSAY

(75) Inventors: Tero Soukka, Turku (FI); Timo Oikari, Turku (FI); Ville Haaslahti, Turku (FI)

(73) Assignee: Hidex Oy, Turku (FI)

( * ) Notice: Subject to any disclaimer, the term of this patent is extended or adjusted under 35 U.S.C. 154(b) by 12 days.

(21) Appl. No.: 12/085,443

(22) PCT Filed: Nov. 17, 2006

(86) PCT No.: PCT/FI2006/000379

§ 371 (c)(1),
(2), (4) Date: May 23, 2008

(87) PCT Pub. No.: WO2007/060280

PCT Pub. Date: May 31, 2007

(65) Prior Publication Data

US 2009/0081662 A1    Mar. 26, 2009

Related U.S. Application Data

(60) Provisional application No. 60/739,411, filed on Nov. 25, 2005.

(30) Foreign Application Priority Data

Nov. 25, 2005   (FI)  .................................. 20051204

(51) Int. Cl.
*C12Q 1/68*     (2006.01)
*C07H 21/02*    (2006.01)
(52) U.S. Cl. .................. 435/6; 536/24.3; 536/24.33
(58) Field of Classification Search ...................... None
See application file for complete search history.

(56) References Cited

U.S. PATENT DOCUMENTS 6,037,130 A   *   3/2000   Tyagi et al. .................... 435/6

(Continued)

FOREIGN PATENT DOCUMENTS

WO     WO 98/43072     10/1998

(Continued)

OTHER PUBLICATIONS

Tyagi et al., "Wavelength-Shifting Molecular Beacons," 18 *Nature Biotech.* 1191-1196 (2000).

(Continued)

*Primary Examiner*—Young J Kim
(74) *Attorney, Agent, or Firm*—James C. Lydon

(57) ABSTRACT

A homogenous bioassay including a first group including an acceptor which is a short lifetime fluorescent compound capable of energy transfer, and a second group including a quencher which is capable of energy transfer from an acceptor. The increase or decrease of the acceptor's fluorescence resulting from lengthening or shortening of the distance between the acceptor and quencher is measured. The bioassay also includes a third group including a donor for energy transfer to the acceptor, which donor is an up-conversion fluorescent compound, a long-lifetime fluorescent compound or an electrogenerated luminescent compound. The first group includes a tag, the third group includes a binder having a high affinity for binding to the tag. Fluorescence of the acceptor is brought about by exciting the donor resulting in energy being transferred from the donor to the acceptor.

23 Claims, 9 Drawing Sheets

U.S. PATENT DOCUMENTS

| | | |
|---|---|---|
| 6,768,000 B1 | 7/2004 | Nardone |
| 2005/0007119 A1 | 1/2005 | Belakov et al. |
| 2005/0054573 A1 | 3/2005 | Werner et al. |
| 2005/0170442 A1 | 8/2005 | Kupcho et al. |
| 2007/0059690 A1* | 3/2007 | Islam et al. .................... 435/6 |

FOREIGN PATENT DOCUMENTS

| | | |
|---|---|---|
| WO | WO 00/06778 | 2/2000 |
| WO | WO 2004/086049 | 10/2004 |

OTHER PUBLICATIONS

Karvinen et al., "Homogeneous Time-Resolved Fluorescence Quenching Assay (LANCE) for Caspase-3," 7 *J.Biomolecular Screening* 223-231 (2002).

Fang et al., "Designing a Novel Molecular Beacon for Surface-Immobilized DNA Hybridization Studies," 121 *J.Am.Chem.Soc.* 2921-2922 (1999).

Patent Office Communication in counterpart European application 06 820 060 (Mar. 31, 2009).

* cited by examiner

HOMOGENEOUS LUMINESCENCE BIOASSAY

This application is a U.S. National Stage of International Application PCT/FI2006/00379, filed Nov. 17, 2006, which claims benefit under 35 U.S.C. §119 of U.S. provisional application 60/739,411, filed Nov. 25, 2005 and Finnish patent application 20051204, filed Nov. 25, 2005.

FIELD OF THE INVENTION

This invention relates to measurement of biological activity or its modulation or analyte concentration using a luminescence energy transfer based homogeneous bioassay.

BACKGROUND OF THE INVENTION

The publications and other materials used herein to illuminate the background of the invention, and in particular, cases to provide additional details respecting the practice, are incorporated by reference.

A number of assays based on bioaffinity binding reactions or enzymatically catalyzed reactions have been developed to analyze biologically important compounds or their activity or their biological effect or its modulation from various biological samples (such as serum, blood, plasma, saliva, urine, faeces, seminal plasma, sweat, liquor, amniotic fluid, tissue homogenate, ascites, etc.), samples in environmental studies (waste water, soil samples), industrial processes (process solutions, products) and compound libraries (screening libraries which may comprise organic compounds, inorganic compounds, natural products, extracts of biological sources, biological proteins, peptides, or nucleotides, etc.). Some of these assays rely on specific bioaffinity recognition reactions, where generally natural biological binding components are used to form the specific binding assay (with biological binding components such as antibodies, natural hormone binding proteins, lectins, enzymes, receptors, DNA, RNA, LNA or PNA) or artificially produced binding compounds like genetically or chemically engineered antibodies, molded plastic imprint (molecular imprinting), other assays rely on activity or modulation of the activity of compounds present in sample or added into reaction (e.g. biologically active enzymes, chemical compounds with activity on biological molecules, enzyme substrates, enzyme activators, enzyme inhibitors, enzyme modulating compounds) and so on. Such assays generally rely on a label or a combination of multiple labels generating signals to quantitate the formed complexes after recognition and binding reaction. In heterogeneous assays a separation step (separations like precipitation and centrifugation, filtration, affinity collection to e.g. plastic surfaces such as coated assay tubes, slides or microparticles, solvent extraction, gel filtration, or other chromatographic systems, and so on) is generally required before e.g. the free or bound fraction of the label signal can be measured. In homogeneous assays the signal of the label or labels is modulated due to binding reaction or enzymatic activity or other measured effect and no separation step is needed before measurement of the label signal. Both in heterogeneous and homogeneous assays the measurement of the label signal from free or bound fraction of the label generally enables the calculation of the analyte or activity in the sample directly or indirectly, generally through use of a set of standards to which unknown samples are compared. Different binding assay methods have been reviewed recently in Principles and Practice of Immunoassay, 2nd ed., C. P. Price and D. J. Newman, eds., Palgrave Macmillan, Hampshire, UK, 2001; and The Immunoassay Handbook, 2nd ed. David Wild, ed., Nature Publishing Group, New York, N.Y., 2001.

High-affinity Binders to Small Molecules

Avidin (Green, N. M.; *Adv. Protein Chem.* 1975; 29: 85-133; and Wilcheck, M. and Bayer E. A. Methods in Enzymology: Avidin-Biotin Technology, 1990 Vol. 184) and streptavidin (Chaiet, I. and Wolf, F. J. The properties of streptavidin, a biotin-binding protein produced by Streptomycetes. *Arch. Biochem. Biophys.* 1964; 106: 1-5) have high binding affinity to biotin, the affinity being one of the strongest known reversible binding interactions. Both avidin and biotin and their derivatives are widely employed in biotechnology (Diamandis E P, Christopoulos T K. The biotin-(strept)avidin system: principles and applications in biotechnology. *Clin Chem.* 1991; 37: 625-636). The most commonly used high-affinity binders are monoclonal antibodies selected from hybridoma cultures and polyclonal antibodies. In addition to antibodies, there are numerous other examples of rapid and tight binders to small molecules, and in vitro evolution enables production of high affinity binders against almost any molecule (Lipovsek D, Pluckthun A. In-vitro protein evolution by ribosome display and mRNA display. *J Immunol Methods.* 2004; 290: 51-67; Pini A, Bracci L. Phage display of antibody fragments. *Curr Protein Pept Sci.* 2000; 1: 155-169; and Hoogenboom H R. Overview of antibody phage-display technology and its applications. *Methods Mol Biol.* 2002; 178: 1-37). Single-chain antibody mutants against small molecule fluorescent dye fluorescein (Boder E, Midelfort K, and Wittrup K; Directed evolution of antibody fragments with monovalent femtomolar antigen-binding affinity, *Proc Natl Acad Sci USA* 2000; 97: 10701-10705) have been evolved in vitro with antigen-binding equilibrium dissociation constant $K_d$=48 fM and slower dissociation kinetics (half-time >5 days) than those for the streptavidin-biotin complex.

Fluorescence Resonance Energy Transfer

Fluorescence resonance energy transfer (FRET) (Förster, T. Intermolecular energy migration and fluorescence. Ann. Physik 1948; 2, 55-75.) (or Förster resonance energy transfer) describes an energy transfer mechanism between two fluorescent molecules or between a fluorescent and a non-luminescent molecule. A fluorescent donor is excited at its specific fluorescence excitation wavelength. By a long-range dipole-dipole coupling mechanism, this excited state is then nonradiatively transferred to a second molecule, the acceptor, which is luminescent and can emit at its specific emission wavelength, or the quencher, which is non-luminescent or luminescent. The donor returns to the electronic ground state. The mechanism is widely employed in biomedical research (reviewed by Selvin P R The renaissance of fluorescence resonance energy transfer. Nat Struct Biol 2000; 7: 730-734; and Lakowicz, J. Principles of fluorescence spectroscopy, $2^{nd}$ edition. Plenum Press, New York, 1999).

The FRET efficiency is determined by the distance between the donor and the acceptor, the spectral overlap of the donor emission spectrum and the acceptor absorption spectrum, and the relative orientation of the donor emission dipole moment and the acceptor absorption dipole moment. The FRET efficiency E depends on the donor-to-acceptor distance r with an inverse 6th order law defined by $$E=1/(1+(r/R_0)^6)$$

with $R_0$ being the Förster distance of this pair of donor and acceptor at which the energy transfer efficiency is 50%. The Förster distance depends on the overlap integral of the donor emission spectrum with the acceptor absorption spectrum and their mutual molecular orientation.

Self-quenched Fluorescent Oligomers and Oligomeric Substrates

Biooligomer derivatives, for example oligopeptide, oligonucleotide and oligosaccharide derivatives, containing both a fluorescent moiety and a quencher moiety covalently attached typically to different ends of the same oligomer molecule, are employed to measure hydrolysation or cleavage of the oligomer upon for example enzymatic or chemical activity. The hydrolysis and cleavage, resulting in increase in the distance between a fluorescent moiety and a quencher moiety, are accompanied by an increase in the fluorescence due to disruption of the intramolecular quenching of the fluorescent moiety. The spectral properties of the moieties do not necessarily need to be consistent with an energy transfer mechanism according to Förster requiring spectral overlapping between emission spectra of the fluorescent moiety (donor) and excitation spectra of the quencher moiety.

Self-quenched oligopeptide substrates, also called fluorogenic substrates, and their applications have been described e.g. by Lottenberg R, Christensen U, Jackson C M, Coleman P L Assay of coagulation proteases using peptide chromogenic and fluorogenic substrates. *Methods Enzymol.* 1981; 80: 341-61; and by Lew R A, Tochon-Danguy N, Hamilton C A, Stewart K M, Aguilar M I, Smith A I. Quenched fluorescent substrate-based peptidase assays. *Methods Mol Biol.* 2005; 298: 143-150. The use of specific quenched fluorescent oligopeptide substrates provides a rapid and sensitive method to measure peptidase activity, and is readily adaptable to high-throughput screening of potential peptidase inhibitors. A high throughput assay based on a peptide labelled with both a fluorescent europium chelate and a quencher has been described by Karvinen J, Hurskainen P, Gopalakrishnan S, Burns D, Warrior U, Hemmila I. Homogeneous time-resolved fluorescence quenching assay (LANCE) for caspase-3. *J Biomol Screen.* 2002; 7: 223-231. The principle of a peptidase assay based on quenched fluorescent substrate is illustrated in FIG. 1. In an intact fluorescent substrate the fluorescent label is quenched by the quencher, but when a peptidase cleaves the substrate the distance between the fluorescent label and the quencher increases recovering the fluorescence of the fluorescent compound. The measured signal is increased upon cleavage of the substrate.

Cleavage of the peptide by caspase-3 separates the quencher from the chelate and thus recovers fluorescence of europium chelate. A similar assay is possible by using a long-lifetime fluorescent metal-porphyrin label (O'Riordan T C, Hynes J, Yashunski D, Ponomarev G V, Papkovsky D B. Homogeneous assays for cellular proteases employing the platinum(II)-coproporphyrin label and time-resolved phosphorescence. *Anal Biochem* 2005; 342: 111-119). Phosphorescent platinum(II) coproporphyrin label was evaluated for the detection of cellular proteases by time-resolved fluorescence in homogeneous format. An octameric peptide containing the recognition motif for the caspase-3 enzyme was dual labelled with a new maleimide derivative of phosphorescent platinum(II) coproporphyrin label and with the non-luminescent quencher dabcyl. Donor-acceptor energy transfer and fluorescence quenching based assays have been described also for other enzymes: a protease related to apoptosis, helicase involved in DNA unwinding, and phosphatase having an important role in cellular signaling cascades (Karvinen J, Laitala V, Makinen M L, Mulari O, Tamminen J, Hermonen J, Hurskainen P, Hemmila I. Fluorescence quenching-based assays for hydrolyzing enzymes. Application of time-resolved fluorometry in assays for caspase, helicase, and phosphatase. *Anal Chem* 2004; 76: 1429-1436).

A cleavage assay can also be constructed using e.g. a terbium-chelate donor labelled streptavidin and using a biotinylated peptide substrate containing dabcyl as non-luminescent quencher or fluorescein as a luminescent acceptor at the other end of the peptide sequence. A similar cleavage assay using europium-chelate and donor labelled biotinylated peptide and streptavidin conjugate of XL665 luminescent acceptor is described in Kennedy M E, Wang W, Song L, Lee J, Zhang L, Wong G, Wang L, Parker E. Measuring human beta-secretase (BACE1) activity using homogeneous time-resolved fluorescence. *Anal Biochem.* 2003; 319: 49-55.

The principle of an assay with non-luminescent quencher is illustrated in FIG. 2, where the intact peptide contains both biotin and quencher moieties and is capable to bind to a fluorescent conjugate of streptavidin and quenches the fluorescence of the fluorescent label. When the peptide is cleaved the biotin and quencher moieties are separated and the quencher label is unable to bind to streptavidin and the fluorescence of the fluorescent label is not affected. Thus, the measured signal is increased upon cleavage of the substrate, because the cleavage prevents the quenching of the fluorescent label. The concentration of the fluorescent conjugate of streptavidin must be carefully adjusted because an excess of it results in a significant increase in the background signal.

FIG. 3 illustrates an assay based on a luminescent acceptor, where the substrate contains both biotin and acceptor moieties and is capable to bind to a donor conjugate of streptavidin. The sensitized acceptor emission is dependent on the proximity of donor and acceptor and only the acceptor present in an intact substrate is able to bind to streptavidin. Upon cleavage of the substrate the measured signal is decreased. The donor conjugate of streptavidin can be used in excess because signal without significant increase in the background signal. This method is used by Invitrogen (Carlsbad, Calif.; www.invitrogen.com) in their Lanthascreen concept based on terbium-chelate labelled streptavidin and biotinylated substrate labelled with fluorescein (http://www.invitrogen.com/-downloads/F-13279_LanthaScreen_Poster.pdf). The time-resolved FRET value is determined as a ratio of the FRET-specific signal measured with a 520 nm filter to that of the signal measured with a 495 nm filter, which is specific to terbium-chelate.

Fluorescence quenching assay based on an electrochemiluminescent label and luminescence quenching based on energy transfer is described in Spehar A M, Koster S, Kulmala S, Verpoorte E, de Rooij N, Koudelka-Hep M. The quenching of electrochemiluminescence upon oligonucleotide hybridization. *Luminescence* 2004; 19: 287-95. Interaction between electrochemically excited Ru(bpy)$_3^{2+}$ and Cy5 in a hybridization assay on a chip was studied. The 3' end of an oligonucleotide was labelled with Ru(bpy)$_3^{2+}$ and the 5' end of a complementary strand with Cy5. Upon the hybridization, the electrochemiluminescence (ECL) of Ru(bpy)$_3^{2+}$ was efficiently quenched by Cy5 with a sensitivity down to 30 nmol/l of the Cy5-labelled complementary strand. The quenching efficiency is calculated to be 78%.

Quantitative 5'-nuclease based polymerase chain reaction assay (TaqMan; Applied Biosystems, Foster City, Calif.) is a nucleic acid sequence detection method wherein a single-stranded self-quenching oligonucleotide probe, containing both a fluorescent moiety and a quencher moiety, is cleaved by the nuclease action of nucleic acid polymerase upon hybridisation during nucleic acid amplification (Lie Y S, Petropoulos C J. Advances in quantitative PCR technology: 5' nuclease assays. *Curr Opin Biotechnol.* 1998; 9: 43-48; and Orlando C, Pinzani P, Pazzagli M. Developments in quantitative PCR. *Clin Chem Lab Med.* 1998; 36: 255-269).

Molecular beacons are single-stranded oligonucleotide hybridization probes that form a stem-and-loop structure (Tan W, Wang K, Drake T J. Molecular beacons. *Curr Opin Chem Biol.* 2004; 8: 547-553; and Tan W, Fang X, Li J, Liu X. Molecular beacons: a novel DNA probe for nucleic acid and protein studies. *Chemistry* 2000; 6: 1107-1111). The loop contains a nucleic acid probe sequence that is complementary to a target sequence, and the stem is formed by the annealing of complementary arm sequences that are located on either side of the probe sequence. A fluorescent moiety is covalently linked to the end of one arm and a quencher is covalently linked to the end of the other arm. Due to the proximity of a fluorescent moiety and a quencher moiety molecular beacons do not fluoresce when they are free in solution. However, when they hybridize to a complementary nucleic acid strand containing a target sequence they undergo a conformational change increasing the distance between fluorescent moiety and the quencher moiety that enables the probe to fluoresce. In the absence of a complementary target sequence, the beacon probe remains closed and there is no fluorescence due to intramolecular quenching.

Selective cleavage of internucleotide bonds of self-quenched single-stranded oligonucleotide probes, which contain one or more ribonucleotides, by RNase H upon double-stranded helix formation subsequent to hybridisation to target is another method of target sequence detection (Rizzo J, Gifford L K, Zhang X, Gewirtz A M, Lu P. Chimeric RNA-DNA molecular beacon assay for ribonuclease H activity. *Mol Cell Probes* 2002; 16: 277-283). Yet another method is to use a self-quenched single-stranded oligonucleotide cycling probe, which is cleaved by a double-stranded selective exonuclease upon hybridisation to target sequence. Examples of nuclease-based assays are found in e.g. Till B J, Burtner C, Comai L, Henikoff S. *Nucleic Acids Res.* 2004; 32: 2632-2641.

Self-quenched fluorescent probes are also used to monitor nucleic acid amplification process in a thermal cycler; for example in quantitative polymerase chain reaction the amount of fluorescence at any given cycle, or following cycling, depends on the amount of specific product. The self-quenched single-stranded fluorescent probes, for example molecular beacons or Taqman probes, bind to the amplified target following each cycle of amplification and the resulting signal upon hybridisation, and in case of Taqman probes upon cleavage, is proportional to the amount of the amplified oligonucleotide sequence. Fluorescence is measured during each annealing step when the molecular beacon is bound to its complementary target or after elongation step when the Taqman probe is cleaved. The information is then used during quantitative PCR or RT-PCR (reverse transcriptase PCR) experiments to quantify initial copy number of amplified target nucleic acid sequence. For endpoint analysis, PCR or RT-PCR reactions containing molecular beacons can be run on any 96-well thermal cycler and then read in a fluorescence reader.

Fluorescent oligosaccharide substrates and their use in fluorescence quenching assay has been described in Cottaz S, Brasme B and Driguez H, A fluorescence-quenched chitopentaose for the study of endo-chitinases and chitobiosidases. *Eur. J. Biochem.* 2000; 267: 5593-5600.

Non-fluorescent acceptor labels and their use in fluorescence quenching assays with short-lifetime fluorescent dyes have been described e.g. in U.S. Pat. No. 6,828,116.

Ribonuclease detection using dual-labelled quenched fluorescent oligonucleotide containing both short-lifetime fluorescent dye and non-luminescent acceptor has been described in US 2004/0137479.

Fluorescent quenching assay for protein kinase based on fluorescent labelled substrate and phosphate specific binder labelled with non-luminescent acceptor is described in US 2004/024946.

Fluorescence quenching assays based on both fluorescent streptavidin-coated microspheres and conjugates of small-molecule fluorescent dyes in combination with both non-luminescent acceptor dye and quencher polymer have been described in US 2003/0054413.

Fluorescence quenching assay based fluorescent streptavidin-coated microsphere and biotinylated non-luminescent acceptor labelled protease substrate for measurement of protease activity has been described in US 2005/0014160.

Protease activity assay based on dual-labelled fluorescent protein substrate containing binding moiety for purification and separation is described in US 2005/0214890.

In all of the aforementioned examples a fluorescent moiety or a fluorescent compound (donor) is used in combination with either non-luminescent compound (quencher) or luminescent compound (acceptor), respectively, and the donor compound is capable of transferring energy either to a quencher or to an acceptor, respectively, said energy transfer being dependent on the distance between the donor and quencher or acceptor.

In all cases the donor is excited directly by light or electrochemically and, in case of a non-luminescent acceptor, it's the donor's own light emission (fluorescence) is measured or in case of luminescent acceptor, the sensitized emission of an acceptor (originating from energy transfer) is measured.

Homogeneous Bioassay Technologies

Homogeneous assay methods (Ullman E F, *J Chem Ed* 1999; 76: 781-788; Ullman, E F, *J Clin Ligand Assay* 1999; 22: 221-227) based on photoluminescence have received much attention, since several types of physical and chemical interactions can be employed to modulate the emission of photoluminescent labels due to formation of specific immunological complexes. The commonly employed methods are based on polarization of the emitted light or nonradiative energy-transfer between two photoluminescent compounds or between a photoluminescent and a non-luminescent compound (Hemmilä I, *Clin Chem* 1985; 31: 359-370). Fluorescence properties of two fluorescent compounds were employed in a homogeneous immunoassay in late 1970's when Ullman et al. demonstrated, that fluorescence energy transfer between a fluorescein donor and tetramethylrhodamine acceptor pair could be employed to construct both competitive and non-competitive immunoassays (Ullman E F et al. J Biol Chem 1976; 251: 4172-4178; Ullman E F & Khanna P L, *Methods Enzymol* 1981; 74: 28-60). The energy transfer was measured from decrease in the fluorescence of the donor, which limited further improvements in sensitivity. Increase in the fluorescence of the acceptor was not practicable, since only a little increase in a sensitized acceptor emission could be observed over autofluorescence, light scattering or absorbance of biological sample matrices and the direct emission of the donor at acceptor-specific wavelength.

Many compounds and proteins present in biological fluids or serum are intrinsically fluorescent, and the use of conventional fluorophores leads to serious limitations of sensitivity (Wu P and Brand L, *Anal Biochem* 1994; 218:1-13). Another major problem with homogeneous fluorescence techniques is the inner filter effect and the variability of the optical properties of a sample. Sample dilution has been used to correct this drawback, but always at the expense of analytical sensitivity. Feasibility of fluorescence energy transfer in immunoassays was significantly improved when fluorescent lanthanide cryptates and chelates with long-lifetime emission and large Stokes' shift were employed as donors in the 1990's (Mathis G, *Clin Chem* 1993; 39: 1953-1959; Selvin P R et al., *Proc Natl Acad Sci USA* 1994; 91: 10024-10028; Stenroos K et al., Cytokine 1998; 10:495-499; WO 98/15830; U.S. Pat. No. 5,998,146; WO 87/07955). Feasibility of the label technology in dissociation reactions, e.g. cleavage assays has also been described (Karvinen J et al., *J Biomol Screen* 2002; 7: 223-231).

Time-resolved fluorescence detection of sensitized emission allowed elimination of autofluorescence (Soini E and Kojola H Time-resolved fluorometer for lanthanide chelates—a new generation of nonisotopic immunoassays. *Clin Chem* 1983; 29: 65-68). Dual signal ratio measurement (U.S. Pat. No. 5,527,684; Mathis, G, *Clin Chem* 1993; 39: 1953-1959) corrected the variability of optical properties of the sample in homogeneous assay. Fluorescence of the compounds and proteins present in biological fluids has a short lifetime and the use of long-lifetime labels combined with time-resolved detection of the sensitized (prolonged lifetime) acceptor emission allowed minimization of the assay background and improved signal to background ratio. The variability of absorption of excitation light at 337 nm was corrected by measuring the emission of the donor at 620 nm and using the ratio of the energy transfer signal at 665 nm and the emission at 620 nm to generate a quantity that is independent of the optical properties of the serum sample. Homogeneous time-resolved FRET based bioaffinity assays using long-lifetime fluorescent nanoparticles have been described in WO 02/044725 and by Kokko L, Sandberg K, Lövgren T and Soukka T, Europium(III) chelate-dyed nanoparticles as donors in a homogeneous proximity-based immunoassay for estradiol *Anal Chim Acta* 2004; 503: 155-162. In the latter publication it is described that multiple lanthanide chelates inside a single particulate can participate simultaneously in energy transfer to a single acceptor. However, still only a small part of the lanthanide chelates inside the entire particulate can participate in an energy transfer to a single acceptor and thus the entire fluorescence of a particulate label cannot be quenched by a single acceptor moiety. The same problem is also encountered when lanthanide chelates are incorporated in a solid phase.

Separation-free assay technologies based on confocal detection of photoluminescent labels bound on particulate carriers have been introduced as an alternative to real homogeneous assays (Saunders G C et al., *Clin Chem* 1985; 31:2020-2023; Frengen J et al., *Clin Chem* 1993; 39:2174-2181; Fulton R J et al., *Clin Chem* 1997; 43:1749-1756). In recent years, the technology has been developed, and some novel carrier-based immunoassays can be considered as homogeneous assays, since they are practically similar to perform (Hänninen P et al., *Nat Biotechnol* 2000; 18:548; U.S. Pat. No. 5,891,738; Schaertl S et al., *J Biomol Screen* 2000; 5:227-238), although the actual signal of the label is not modulated, but the unbound labelled component is spatially excluded from measurement. These assays are otherwise comparable to homogeneous assays, but measurement is relatively slow, since carrier particles have to be either actively scanned or passively diffuse to a focal point, and a signal associated to several carrier particles is required for reliable measurement (Waris M E et al., *Anal Biochem* 2002; 309: 67-74). To avoid sterical hindrance in binding at least one of the labels, preferably both labels of a label-pair should be of small molecular size.

In most of the conventional homogeneous fluorescence assay technologies, the performance has still severe limitations: the sensitivity is limited by interferences from matrix components and optical properties of matrices, e.g. urine, saliva, serum, plasma or whole blood, to fluorescence yield and level of background, and by the attainable degree of fluorescence modulation, e.g. quenching, enhancement, energy transfer or polarization (Hemmilä I, *Clin Chem* 1985; 31: 359-370). In practice, only wavelengths in the range 600 to 1100 nm, or more preferably in the near infrared, in a wavelength range 650 to 950 nm, are practicable when a whole blood sample is employed (Chance B, Photon Migration in Tissues, pp. 206; Kluwer Academic/Plenum Publishers, 1990, New York).

Homogeneous luminescence-based whole-blood assay based on FRET and up-conversion photoluminescence is described in WO 2004/086049. Both the excitation and the measurement of sensitized acceptor emission have to be performed at far-red and infrared wavelengths where the sample is transparent, in this case at wavelengths 900-1000 nm and approximately 580-640 or 690-750 nm.

OBJECT AND SUMMARY OF THE INVENTION

One object of the present invention is to provide a homogenous bioassay for use in measurement of biological activity, its modulation or analyte concentration of a sample.

The present invention provides a homogenous bioassay for use in measurement of biological activity, its modulation or analyte concentration of a sample, said bioassay comprising
i) a first group comprising an acceptor, which acceptor is a short lifetime fluorescent compound capable of energy transfer, and
ii) a second group comprising a quencher, which quencher is capable of energy transfer from an acceptor, and
the increase or decrease, respectively, of fluorescence of said acceptor due to the decrease or increase, respectively, of energy transfer from said acceptor to said quencher resulting from lengthening or shortening, respectively, of the distance between said acceptor and quencher is measured.

Characteristic for the Invention is that the Bioassay Comprises
iii) a further third group comprising a donor for energy transfer to said acceptor, which donor is an up-conversion fluorescent compound, a long-lifetime fluorescent compound or an electrogenerated luminescent compound; and
said first group comprises a tag, said third group comprises a binder, and said binder has a high affinity for binding to said tag; and
the fluorescence of said acceptor is brought about by exciting the donor resulting in energy being transferred from the donor to the acceptor.

DETAILED DESCRIPTION OF THE INVENTION

Definitions

Figure 1A:
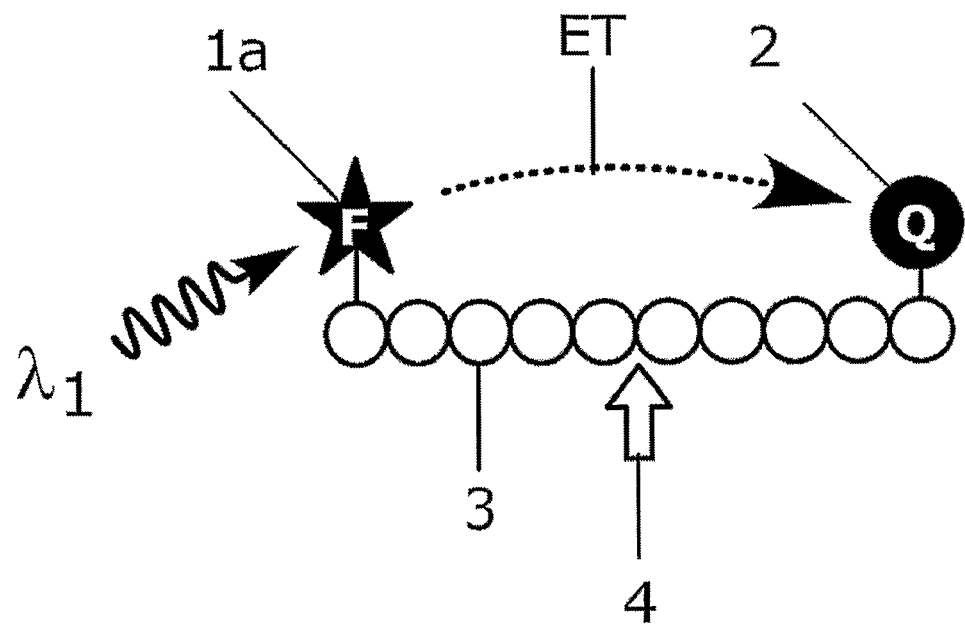
FIG. 1 illustrates the use of dual-labelled oligomer substrate in a prior art cleavage bioassay.

In this disclosure, the term "bioassay" shall be understood to refer to cleavage assays, conformation change assays, and dissociation and association assays. In cleavage assays an intact dual labelled oligomer is cleaved and the distance between two or more parts of the dual labelled oligomer increases; one part of the oligomer contains the fluorescent compound and another quencher compound. In conformation change assays, such as molecular beacon type assays, the conformation of an oligomer is changed due to, for example, binding of modulating compound, increasing the distance between the fluorescent compound and the quencher compound attached to different positions of the oligomer. In dissociation and association assays, for example nucleic acid hybridization assays, the distance between the two labelled oligomers decreases or increases, respectively, upon binding, wherein one oligomer is labelled with a fluorescent compound and another with a quencher compound.

The term "homogeneous bioassay" shall be understood to cover bioassays requiring no separation steps. Single or multiple steps of each; addition of reagents, incubation and measurement are the only steps required. The term "separation step" shall be understood to be a step where a labelled bioassay reagent bound onto a solid-phase, such as for example a microparticle or a microtitration well, is separated and physically isolated from the unbound labelled bioassay reagent; for example the microtitration well is washed (liquid is taken out and, to improve the separation, additional liquid is added and the well emptied) resulting in separation of the solid-phase bound labelled bioassay reagent from the labelled bioassay reagent not bound onto the solid-phase.

The term "fluorescence" shall be understood to cover photoluminescence, i.e. luminescence excited by light, fluorescence, including delayed fluorescence with microsecond or millisecond fluorescence lifetime, ionic photoluminescence, up-conversion based anti-Stokes photoluminescence, and phosphorescence. In addition, the term shall cover electro-generated luminescence and electrochemiluminescence.

The term "fluorescent label" or "fluorescent compound" shall be understood to cover dye molecules, proteins, polymers, particles, dyed particles and phosphors, which express fluorescence.

The terms "acceptor" and "donor" shall be understood to cover fluorescent compounds, which participate in energy transfer processes with another fluorescent compound or a non-luminescent compound.

The terms "non-luminescent" and "non-fluorescent" shall be understood as property of a light absorbing compound not to produce any or a significant amount of luminescence when excited and relaxing from the excited-state. In contrast to luminescent compounds, the excited-state energy of a non-luminescent compound is predominantly relaxed via non-radiative pathways, typically producing heat instead of light. The fluorescence quantum yield of a non-luminescent compound is very poor, typically below 5 percent. Examples of non-luminescent compounds are quencher compounds, which can efficiently participate in energy transfer from a fluorescent compound, but which do not produce any significant luminescence upon excitation.

The term "tag" shall be understood as a moiety, which can be recognized and bound by a binder. The "binder" means a molecule capable of recognizing and binding to a tag. A tag can be any molecule, but preferably has a molecular weight below 50,000 Da, more preferably less than 20,000 Da, and most preferably less than 5,000 Da. A tag can also be physically the same as or part of the "acceptor" compound. The binder is typically, but not limited to, a protein capable of binding to the tag. Examples of such proteins are antibodies recognizing the tag and streptavidin or avidin when the tag is a biotin moiety. Preferably the binder has a high affinity to the tag, preferably with an affinity constant over $10^7$ l/mol, more preferably over $10^8$ l/mol and most preferably over $10^9$ l/mol. In addition, the interaction between the binder and the tag should be rapid during association and slow during dissociation.

The term "long-lifetime fluorescence" and "long-lifetime fluorescent compound" shall be understood to cover fluorescence and fluorescent compounds having a luminescence lifetime equal to or more than 1 microsecond (the lifetime being calculated as the time wherein luminescence emission intensity decays to the relative value of 1/e, i.e. to approximately 37% of the original luminescence emission intensity). The compounds capable of long-lifetime fluorescence include, but are not limited to, lanthanide chelates, lanthanide-chelate dyed-nanoparticles, lanthanide phosphors and nanophosphors, porphyrins, and porphyrin dyed-nanoparticles.

The term "light" and "excitation light" and "emission light" shall be understood as electromagnetic radiation at wavelengths from 200 nm to 1600 nm. These wavelengths cover ultraviolet, near-ultraviolet, visible, near-infrared and infrared light.

The term "short-lifetime fluorescence" and "short-lifetime fluorescent compound" shall be understood to cover fluorescence and fluorescent compounds with a luminescence lifetime of less than 1 microsecond.

The term "quenched fluorescent substrate" and "quenched fluorescence labelled substrate" shall be understood as a molecule, typically an oligomer, for example an oligopeptide or oligonucleotide, containing both a fluorescent compound and quencher compound capable of energy transfer from a fluorescent compound to quencher compound.

The term "quenched short-lifetime fluorescent substrate" and "quenched long-lifetime fluorescence substrate", respectively, shall be understood as a quenched fluorescent substrate, where the fluorescent compound is a short-lifetime fluorescent compound or a long-lifetime fluorescent compound, respectively.

The terms "quencher", "quencher label" and "quencher compound" shall be understood as non-luminescent or luminescent compound essentially capable of energy transfer from a short-lifetime or long-lifetime fluorescent compound. Typically, but not necessarily, the absorption spectra of the quencher at least partially overlaps with the emission spectra of the donor and the energy transfer from a short-lifetime or long-lifetime fluorescent compound to the quencher compound in proximity can be so effective that the intensity of the fluorescence of the fluorescent compound is decreased over 50%, preferably over 90%, more preferably over 95%, and most preferably over 99%.

The terms "acceptor", "acceptor label" and "acceptor compound" mean luminescent or non-luminescent compounds having typically, but not necessarily, absorption spectra at least partially overlapping with the emission spectra of the donor and essentially capable of energy transfer from the donor.

The terms "donor" and "donor label" shall be understood as fluorescent compounds capable of energy transfer either to an acceptor or quencher compound.

The terms "sensitized emission" and "sensitized acceptor emission" shall be understood as emission of the acceptor label generated by energy transfer from the donor label in proximity upon excitation of the donor label. In case of long-lifetime donor label the sensitized emission has also prolonged fluorescence lifetime. Further, the sensitized emission shall also be understood to cover values of sensitized emission corrected by for example measurement of the donor emission or sample absorbance, or values indicating any ratio of the donor emission and the sensitized emission.

The term "up-conversion fluorescence" and "up-conversion fluorescent compound" means fluorescence produced by and fluorescent compounds converting lower energy incident light to higher energy emitted light. It is also called anti-Stokes fluorescence or anti-Stokes photoluminescence. Anti-stokes photoluminescence material converts low energy light to high energy light. In "up-conversion fluorescence" two or more lower energy photons of the same or different energy are absorbed sequentially, in two or more stages, to generate a single higher energy photon, contrary to simultaneous absorption in two-photon or multi-photon excitation.

The terms "luminescent lanthanide label" and "lanthanide label" shall be understood to include a lanthanide chelate or chelate structure, containing one or more lanthanide ions, an inorganic lanthanide containing phosphor particle, or a polymeric nanoparticle containing either the described lanthanide chelates or the phosphor particles. The lanthanide can represent one single lanthanide element or a combination of several different lanthanide elements.

The term "lanthanide" shall be understood here to be equivalent to "rare earth metal ion" and to include single lanthanide elements and combination of several different lanthanide elements from the following: neodymium, praseodymium, samarium, europium, promethium, gadolinium, terbium, dysprosium, holmium, erbium, thulium, ytterbium and yttrium, especially erbium, praseodymium, thulium, and ytterbium.

The term "up-converting luminescent label" and "up-converting lanthanide label" shall be understood as up-conversion fluorescent compound, i.e. luminescent lanthanide label being able to up-convert a lower energy excitation to a higher-energy emission based on an excitation in two or more stages; meaning that two or more photons are sequentially absorbed to excite the label contrary to simultaneous absorption in two or multi photon excitation. The up-converting lanthanide labels include up-converting lanthanide phosphors and up-converting lanthanide chelates.

The term "up-converting lanthanide chelate" in this context means an up-converting lanthanide label, where a single rare earth ion or a combination of different rare earth ions is chelated to a mono or multinuclear complexing ligand. The ligand may or may not contain a light harvesting structure. The light collection efficiency of individual ions and chelated ligands without a light harvesting structure is poor. Therefore, up-converting rare earth chelates can be designed to contain a ligand with light-harvesting organic or inorganic structures, e.g. another ion, incorporated. The collected energies of two or more photons are transferred one after another by intramolecular nonradiative processes from the singlet to the triplet state of the organic structure, then from the triplet state sequentially to the emissive level of the rare earth ion, which then emits a single photon of characteristic emission.

The term "up-converting lanthanide phosphor" shall be understood as a particulate luminescent lanthanide label capable of up-conversion, wherein a particulate absorbs long wavelength radiation and emits light at shorter wavelength as result of energy pooling of sequential absorption of long wavelength radiation. In certain types of phosphors, a priming dose of energy at shorter wavelength is required to excite and pre-load the phosphor before the up-conversion of long wavelength radiation is possible. The up-converting phosphor can be able to delocalise its excitation from a part or the entire volume of the particulate by internal transfer of energy between similar excited states within the particulate to a single or a few acceptor molecules. This means that a single acceptor can be excited by lanthanides which would otherwise be too far away for energy transfer to be efficient. The diameter of the particulate phosphor is preferable equal or greater than 4 nm and preferably smaller than 10 µm, more preferably smaller than 1 µm.

The term "long-lifetime fluorescent lanthanide label" shall be understood as a long-lifetime fluorescent compound, i.e. a luminescent lanthanide label being able to emit long-lifetime fluorescence upon excitation enabling temporal resolution in fluorescence detection with delay time and gate times equal or greater than 1 microsecond. The long-lifetime lanthanide labels include long-lifetime fluorescent lanthanide phosphors, long-lifetime fluorescent lanthanide-chelate dyed nanoparticles, and long-lifetime fluorescent lanthanide chelates and chelate derivatives. In addition to lanthanide-based compounds the term shall be understood to include platinum and palladium porphyrins and derivatives with similar long-lifetime fluorescence properties.

The term "long-lifetime fluorescent lanthanide chelate" means long-lifetime fluorescent lanthanide label, where a single rare earth ion or a combination of different rare earth ions is chelated to a mono or multinuclear complexing ligand. The ligand may or may not contain a light harvesting structure. The light collection efficiency of individual ions and chelated ligands without light harvesting structure is poor.

The term "long-lifetime fluorescent lanthanide phosphor" and "long-lifetime fluorescent lanthanide-chelate dyed nanoparticle" shall be understood as a particulate luminescent lanthanide label capable of long-lifetime fluorescence. The long-lifetime fluorescent lanthanide phosphor is an inorganic phosphor crystal doped with emissive lanthanide ions. The long-lifetime fluorescent lanthanide-chelate dyed nanoparticle is a polymeric particle dyed with long-lifetime fluorescent lanthanide chelates. The diameter of the particulate phosphor or particle is equal or greater than 4 nm and smaller than 1 μm.

The terms "energy transfer", "fluorescence energy transfer" and "FRET" shall be understood as transfer of excited state energy from donor compound to acceptor or quencher compound in proximity. Typically the energy transfer is based on Förster type fluorescence resonance energy transfer, but especially in case of lanthanide labels other mechanism can be prevalent.

The terms "electrogenerated luminescence" and "electrochemiluminescence" shall be understood as luminescence produced by electrogenerated chemical excitation using an electrode and applying electric current or voltage to electrode. Depending on the electrode where the electrochemical reaction producing luminescence occurs the electrochemiluminescence is called cathodic or anodic electrochemiluminescence. Electrogenerated luminescence compounds are compounds capable of anodic or cathodic electrogenerated luminescence. Examples of such compounds are $Ru(bpy)_3^{2+}$ and its derivatives with red emission and hot electron excited 2,6-bis[N,N-bis(carboxymethyl)-aminomethyl]-4-benzoyl phenol-chelated Tb(III) producing green emission and other lanthanide chelates. Electrogenerated luminescence of lanthanide chelates can also be measured using temporal resolution to improve limit of detection. Further, the electrogenerated luminescence compounds can be embedded in a particulate to amplify the luminescence.

Preferred Embodiments of the Invention

The present invention provides an improved luminescence energy transfer based homogeneous bioassay, suitable for use in measurement of biological activity, its modulation or analyte concentration in a sample. The invention further provides assays which can be carried out by using either long-lifetime luminescent, up-converting luminescent, or electrogenerated luminescent particulate labels as donors to improve signal intensity and limit of detection, which do not need any separation steps and can be measured by fluorometers or other instruments capable of measuring time-resolved fluorescence, up-conversion photo-luminescence, or electrogenerated luminescence, and in case of up-converting luminescent label, which can be performed with a strongly coloured sample.

An improved assay can be achieved by using an arrangement comprising a first group labelled with an energy acceptor and a second group labelled with a quencher. Characteristic to the invention is that an additional third group labelled with an energy donor, wherein the third group is capable to bind to the first group, and wherein the distance between the first group and the second group is observed by excitation of the energy donor of the third group and measuring the emission of the acceptor.

Thus, a typical embodiment of this invention concerns a luminescence energy transfer based homogeneous bioassay comprising a first group labelled with an energy acceptor, a second group labelled with a quencher, and a third group labelled with an energy donor, wherein the energy acceptor is a short-lifetime fluorescent label, said label being able to fluorescence energy transfer to the quencher, the quencher is either a luminescent or a non-luminescent label, the energy donor is a long-lifetime luminescent label, a up-conversion luminescent label, or electrogenerated luminescent label, said label being able to fluorescence energy transfer to acceptor, the first group comprises a tag, the third group comprises a binder, said binder being able to bind said tag, and the increase or decrease, respectively, in energy transfer from the acceptor to the quencher resulting from shortening or lengthening, respectively, of the distance between said labels is observed by exciting the energy donor and measuring the decrease or increase, respectively, in the sensitized emission of the energy acceptor.

According to a typical embodiment of the invention, the assay is performed by contacting the first group and the second group, and optionally the third group, with the sample, the assay is incubated biological activity, for modulation of the biological activity or binding of analyte either to the first or the second group or to both groups, the third group is added into the assay, unless added earlier, the assay is incubated for binding of the first group to the third group, and the energy donor is excited and the sensitized emission of the energy acceptor is measured; the magnitude of said sensitized emission being indicative of the distance between the first group and the second group.

According to one advantageous embodiment, the third group is in the form of particulate, each particulate comprising at least a single said donor and said binder, and preferably comprising multiple of said donors and said binders. One or several, preferable a multitude, of particulates for each assay are used. Preferably the particulate is in the form of microparticle, having a diameter less than 10 micrometers, more preferably in the form of nanoparticle, having diameter less than 400 nanometers, and most preferably in the form of nanoparticle, having diameter less than 100 nanometers and preferably equal to or larger than 4 nm.

The invention provides a unique combination of features to improve homogeneous, non-separation bioassays based on luminescence detection:
1) signal of the assay (sensitized accepter emission) is strictly dependent on the distance between two labels, an acceptor and a quencher, since fluorescence resonance energy transfer is dependent to inverse sixth power of distance,
2) signal of the assay is not significantly generated by acceptor when quencher is in proximity, enabling low background signal independent of donor and acceptor concentrations,
3) signal of the assay can be amplified by using a particulate donor or multiple donors, enabling high signal when acceptor and quencher are not in proximity with each other, yet enabling low background signal when acceptor and quencher are in proximity with each other,
4) signal of the assay based long-lifetime fluorescent donor can be measured free of autofluorescence with temporal resolution, and
5) signal of the assay based up-converting fluorescent donor can be measured free of autofluorescence and scattered excitation light without temporal resolution at a wavelength range where most of the biological samples are practically transparent.

Enzymatic activity of proteases, peptidases and nucleases and effect of possible inhibitors and other modulating compounds to enzymatic activity is commonly measured by using quenched fluorescence labelled peptide or oligonucleotide substrate. Both conventional short-lifetime fluorescent compounds and long-lifetime fluorescent compounds have been employed. Monitoring cleavage of effectively quenched long-lifetime fluorescence labelled substrate by measuring the fluorescence of the fluorescence moiety results in increasing signal with increasing amount of cleaved substrate and typically small amounts of cleaved substrate (i.e. small amount of cleaving agent e.g. enzyme present or the cleaving agent is only weakly active) can be distinguished from background signal using temporal resolution, which eliminates autofluorescence, in measurement. The use of a quenched substrate labelled with short life-time fluorescent compounds produces also increasing signal, but a high background fluorescence does not allow the detection of as small amounts of cleaved substrate as with long-lifetime fluorescence labelled substrates.

The synthesis of long-lifetime fluorescence labelled substrates is, however, more difficult and expensive than short-lifetime fluorescence labelled substrates. In addition long-lifetime fluorescence or up-conversion fluorescence originated from a particulate label cannot be effectively quenched and thus the detection of cleavage of a small amount of substrate is difficult to distinguish from the background although the signal is well measurable. The present invention describes how these limitations can be avoided and the detection of the cleavage of the short-lifetime fluorescence labelled substrates can be significantly improved by detecting the fluorescence of a cleaved short-lifetime fluorescence labelled substrate by energy transfer from a long-lifetime fluorescence or up-conversion fluorescence compound.

The present invention has significant advantages over previously described methods employing particulate labels as it results in an increasing signal with increasing amount of cleaved substrate and enables detection of small amount of cleaved substrate. In addition to the measurement of cleavage of a quenched substrate the present invention can be employed in detection of a change of conformation of a double labelled compound, or association and dissociation of a pair of molecules containing a fluorescent compound and a quencher compound in different parts, capable of binding to each other, of the molecule pair. The use of an up-conversion fluorescence compound as a donor enables also measurement in strongly coloured samples as measurement can be performed using both excitation and emission wavelengths in far-red, near-infrared and infrared—above the major absorption of any biological sample.

Figure 7:
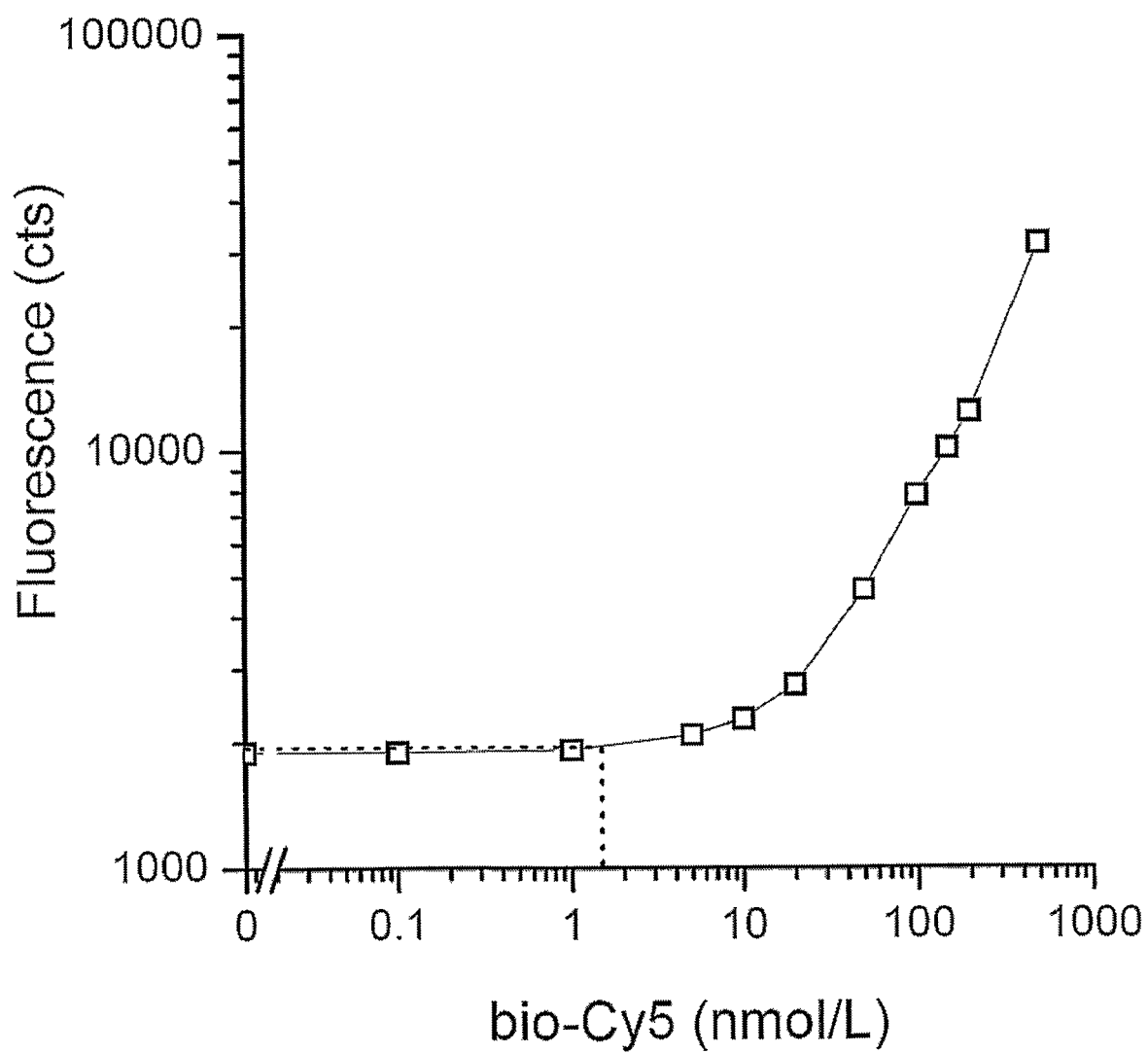
FIG. 7 illustrates measurement of a biotin Cy5 dye conjugate based on the intrinsic short-lifetime fluorescence of the Cy5 dye.

Detectability of intrinsic short lifetime fluorescence of Cy5 dye is illustrated in FIG. 7. The limit of detection is at the concentration of 1.5 nmol/l and low concentrations of the dye cannot be resolved from the background. The limit of detection of a quenched dual-labelled fluorescent substrate containing Cy5 cannot be lower than 1.5 nmol/l even with complete cleavage. In cleavage assays where enzyme activity or its modulation is measured it would be of great advantage to be able to use smaller concentration of substrate to both reduce cost of e.g. enzyme required and decrease the total assay time. The Cy5 (and other short-lifetime fluorescent dye) containing quenched fluorescent substrates are easy to synthesize, inexpensive, and available in large quantities, so improvement of the detection of Cy5 (and other short-lifetime fluorescent dye) based quenched substrates would be of great value.

Surprisingly a very significant improvement can be obtained by combining the detection of the quenched fluorescent substrate with a third label, being either a long-lifetime fluorescent, an anti-Stokes fluorescent, or an electrochemically excited label.

Figure 8:
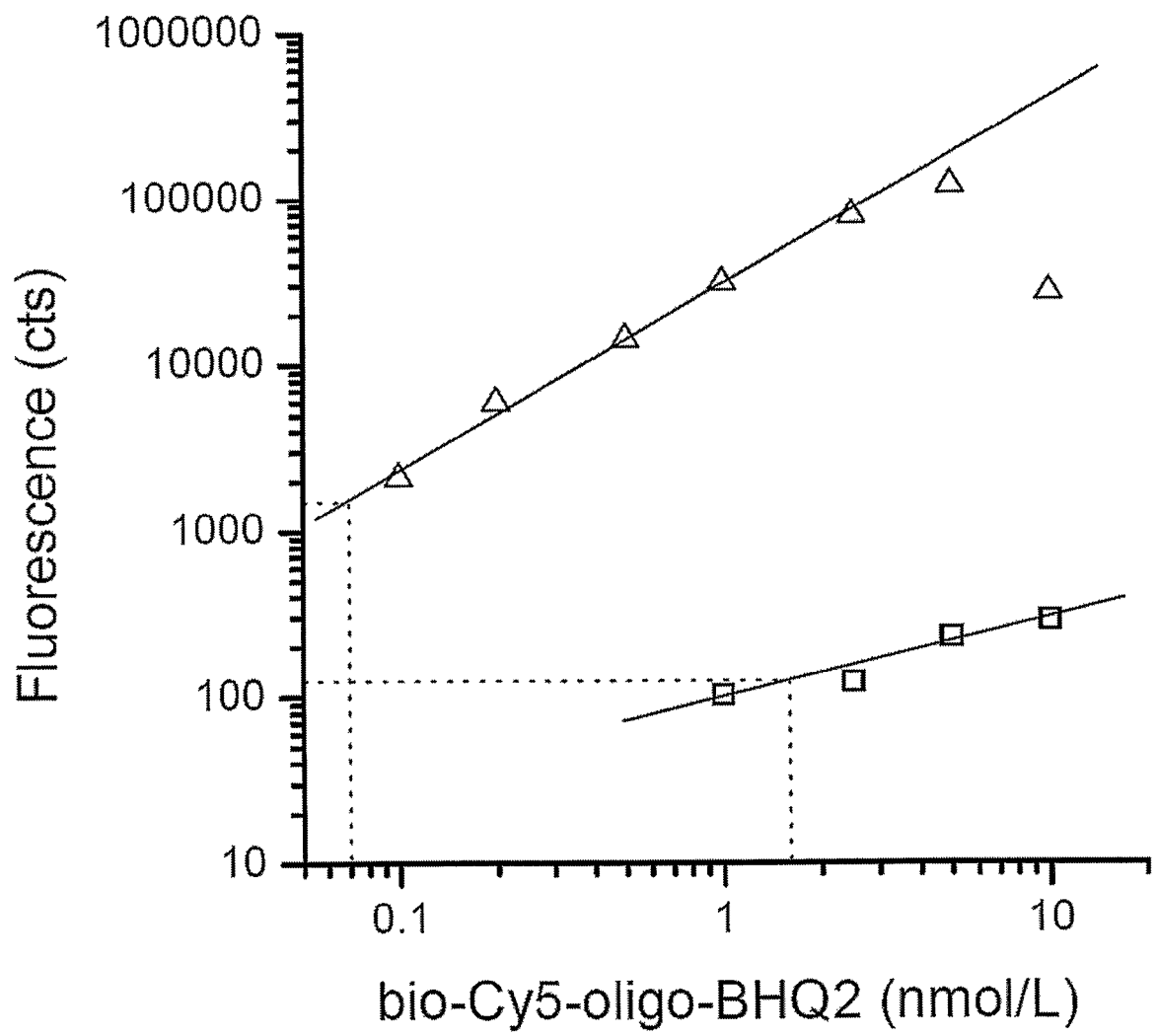
FIG. 8 illustrates measurement of the cleavage of a biotin-Cy5-oligo-BHQ2 conjugate based on the intrinsic short-lifetime fluorescence of the Cy5 dye and based on the sensitized acceptor emission of Cy5 upon excitation of the europium (III) chelate-dyed nanoparticle donor.
Figure 9:
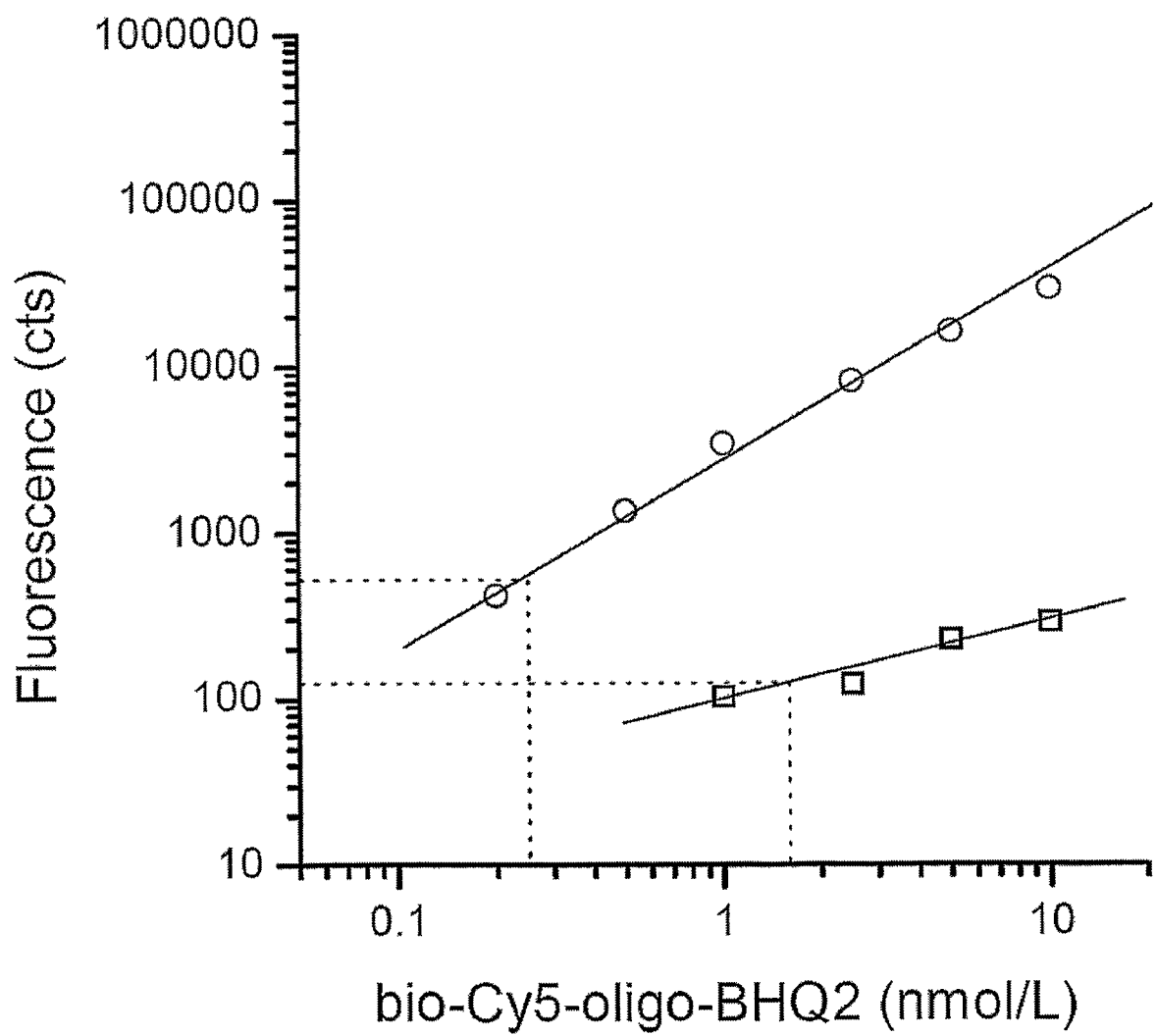
FIG. 9 illustrates measurement of the cleavage of the biotin-Cy5-oligo-BHQ2 conjugate based on the intrinsic short-lifetime fluorescence of the Cy5 dye and based on the sensitized acceptor emission of Cy5 upon excitation of the europium(III) chelate.

Results of a cleavage assay where enzyme activity was measured using a quenched dual-labelled fluorescent substrate containing Cy5 (biotin-Cy5-oligo-BHQ2) are illustrated in FIG. 8. The detectability limit of the cleaved substrate based on intrinsic Cy5 fluorescence is about 1.5 nmol/l as expected. This corresponds to what is known from prior art. However, when the detection is performed according to one embodiment of the current invention, i.e. using europium chelate-dyed streptavidin-coated nanoparticle donor and measuring the long-lifetime sensitized emission of the acceptor Cy5 upon excitation of the donor, the detectability of the same cleaved substrate can be significantly improved down to 0.07 nmol/l. FIG. 9 illustrates the use of a europium(III) chelate labelled streptavidin instead of a europium(III) chelate dyed nanoparticle in a similar cleavage assay, still providing a significant improvement and a limit of detection of approximately 0.25 nmol/l.

According to what is known from prior art a particulate donor label is difficult to be quenched by a single binding event due to the large size of the label. The present invention, however, solves this problem, as a large amount of the fluorescence of the particulate donor label can be transferred to a single acceptor label with can be quenched very efficiently. Thus by using three labels of which one is a particulate label as described in the present invention, the particulate label can be efficiently employed in a fluorescence quenching based assay.

According to what is further known from prior art the particulate lanthanide label is not sensitive to environment in contrast to lanthanide chelates and cryptates. The luminescence of intrinsically fluorescent lanthanide chelates is sensitive to low pH, high concentration of metal chelators, and certain metal ions, for example $Mn^{2+}Cr^+$, $Co^{2+}$, $Fe^{2+/3+}$ and $Cu^{2+}$ can efficiently quench the luminescence of lanthanide chelates. Thus according the present invention, the particulate lanthanide label can be employed in assays where lanthanide chelates are not suitable.

According to the invention the use of a particulate donor provides improved performance but a conventional small molecule long-lifetime fluorescent, an up-conversion fluorescent, or an electrochemically excited fluorescent label can also be employed as a donor to provide a significant improvement over prior art.

A typical assay according to the invention is a homogenous bioassay for use in measurement of biological activity, its modulation or analyte concentration of a sample, said bioassay comprising: a first group comprising an acceptor, which acceptor is a short lifetime fluorescent compound capable of energy transfer, a second group comprising a quencher, which quencher is capable of energy transfer from an acceptor, and the increase or decrease, respectively, of fluorescence of said acceptor due to the decrease or increase, respectively, of energy transfer from said acceptor to said quencher resulting from lengthening or shortening, respectively, of the distance between said acceptor and quencher is measured. The bioassay comprises a further third group comprising a donor for energy transfer to said acceptor, which donor is an up-conversion fluorescent compound, a long-lifetime fluorescent compound or an electrogenerated luminescent compound; said first group comprises a tag, said third group comprises a binder, and said binder has a high affinity for binding to said tag. The fluorescence of said acceptor is brought about by exciting the donor resulting in energy being transferred from the donor to the acceptor.

In preferred embodiments of an assay according to the invention the quencher is non-luminescent. In preferred embodiments of the assay according to the invention the donor is excited either by light or electrochemically.

In some embodiments of the invention the first group and the second group are covalently linked by a covalent linkage, and lengthening of the distance between the acceptor and quencher results from cleavage of the first group from the second group by cleavage of the covalent linkage.

In other embodiments of the invention the first group and/or the second group comprises an oligopeptide, oligonucleotide or oligosaccharide. The cleavage of the first group from the second group is preferably enzymatic.

In further embodiments of the invention the first group and the second group are covalently linked and the covalently linked first and second group comprises different tertiary structures or conformations, and the shortening or lengthening of the distance between the acceptor and quencher results from a change in tertiary structure or conformation. Typically the first group and/or the second group comprises an oligopeptide, oligonucleotide or oligosaccharide.

In still other embodiments of the invention the first group and the second group have an affinity towards each other and the shortening or lengthening, respectively, of the distance between the acceptor and quencher results from association or dissociation, respectively, of said first and second groups. In a preferred embodiment the first group and the second group comprise an oligonucleotide each.

The typical assay according to the invention comprises the steps of
a) bringing the sample, the first group, the second group and optionally the third group, in contact with each other to obtain an assay mixture,
b) allowing the assay mixture to react,
c) bringing the third group in contact with the assay mixture if it was not brought in contact with the assay mixture in step a),
d) allowing the third group to react with the assay mixture if it was brought in contact with the assay mixture in step c),
e) exciting the donor, and
f) measuring the sensitized emission of the acceptor.

In some embodiments of the invention the third group is brought in contact with the assay mixture in step c) and allowed to react with the assay mixture in step d).

In some preferred embodiments of the invention the third group is a particulate comprising one or more donors and one or more binders. Typically the particulate has a diameter of <10 μm, preferably <400 nm, and more preferably <100 nm.

In other preferred embodiments of the invention the third group is incorporated in a solid-surface or a surface coating comprising one or more donors and one or more binders.

The invention also concerns kits for homogenous bioassays according to the invention. A typical kit for a homogenous bioassay according to the invention comprises reagents including
i) a first group comprising an acceptor, which acceptor is a short lifetime fluorescent compound capable of energy transfer, and
ii) a second group comprising a quencher, which quencher is capable of energy transfer from an acceptor, and
iii) a third group comprising a donor for energy transfer to said acceptor, which donor is an up-conversion fluorescent compound, a long-lifetime fluorescent compound or an electrogenerated luminescent compound; and said first group comprises a tag, said third group comprises a binder, and said binder has a high affinity for binding to said tag. The quencher is preferably non-luminescent.

In some preferable embodiments of the kit the first group and the second group are covalently linked, by a covalent linkage. The first group and/or the second groups can comprise an oligopeptide, oligonucleotide or oligosaccharide. In some preferred embodiments the covalently linked first and second group comprise different tertiary structures or conformations. In preferred embodiments the first group and the second group can have an affinity towards each other. In some preferred embodiments the first group and the second group comprise an oligonucleotide each.

In many preferred embodiments of the kit the third group is a particulate comprising one or more donors and one or more binders. The particulate typically has a diameter of <10 μm, preferably <400 nm, and more preferably <100 nm.

In other preferred embodiments of the kit the third group is incorporated in a solid-surface or a surface coating comprising one or more donors and one or more binders.

DESCRIPTION OF THE DRAWINGS

Figure 1B:
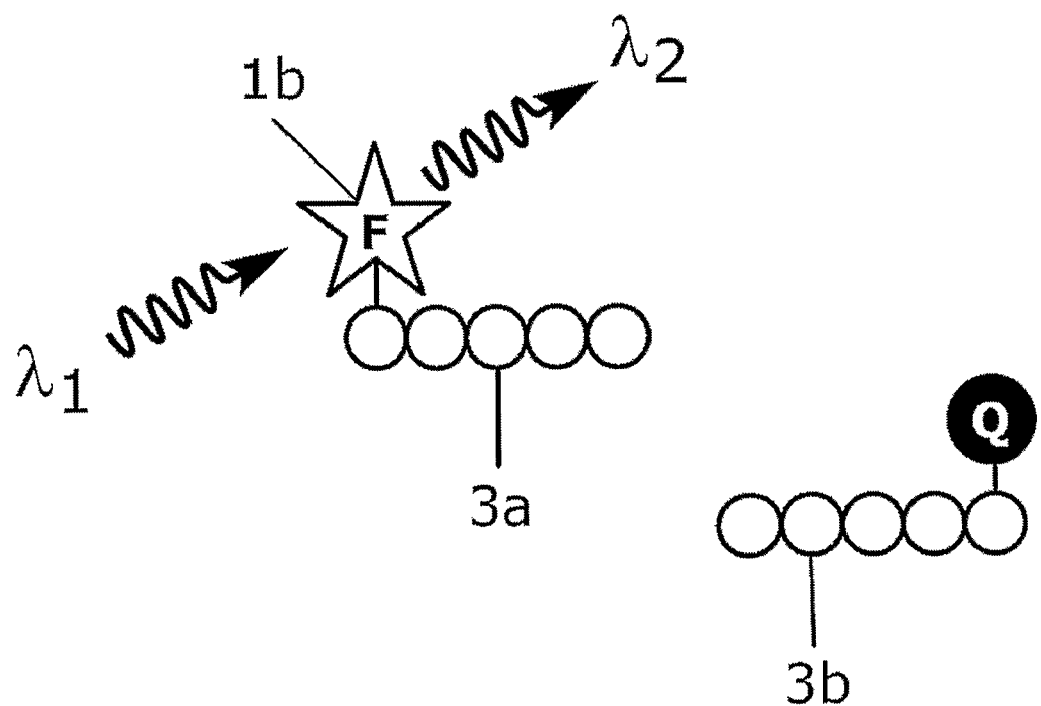

FIG. 1 illustrates the use of a dual-labelled 1a, 2 oligomer substrate 3 in a cleavage bioassay known from prior art. FIG. 1a shows an intact oligomer substrate 3 labelled with fluorescent compound 1a and quencher 2. The intact oligomer 3 has at least one cleavage site 4 where the oligomer 3 can be split to two oligomers or oligomer units. FIG. 1b shows the same oligomer substrate cleaved to two oligomers 3a, 3b. The intact dual-labelled oligomer substrate 3 containing fluorescent compound 1a is not fluorescent upon excitation of the fluorescent compound at excitation wavelength $\lambda_1$, because the excited-state energy of the fluorescent compound is transferred to the non-luminescent quencher 2 and relaxed nonradiatively. The part of the cleaved substrate 3a labelled with fluorescent compound 1b is fluorescent at emission wavelength $\lambda_2$. The amount of fluorescence at emission wavelength $\lambda_2$ is dependent on cleavage of the intact oligomer substrate 3. Energy transfer is abbreviated ET.

Figure 2A:
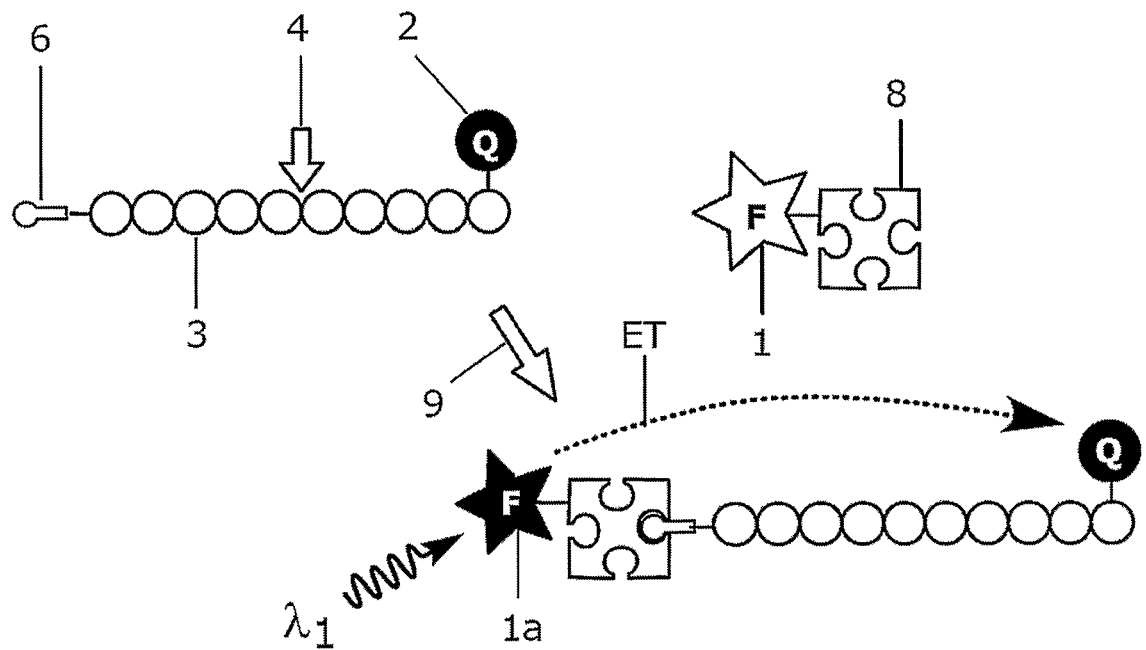
FIG. 2 illustrates the use of quencher labelled tagged oligomer substrate in combination with fluorescent compound labelled binder in another prior art cleavage bioassay.
Figure 2B:
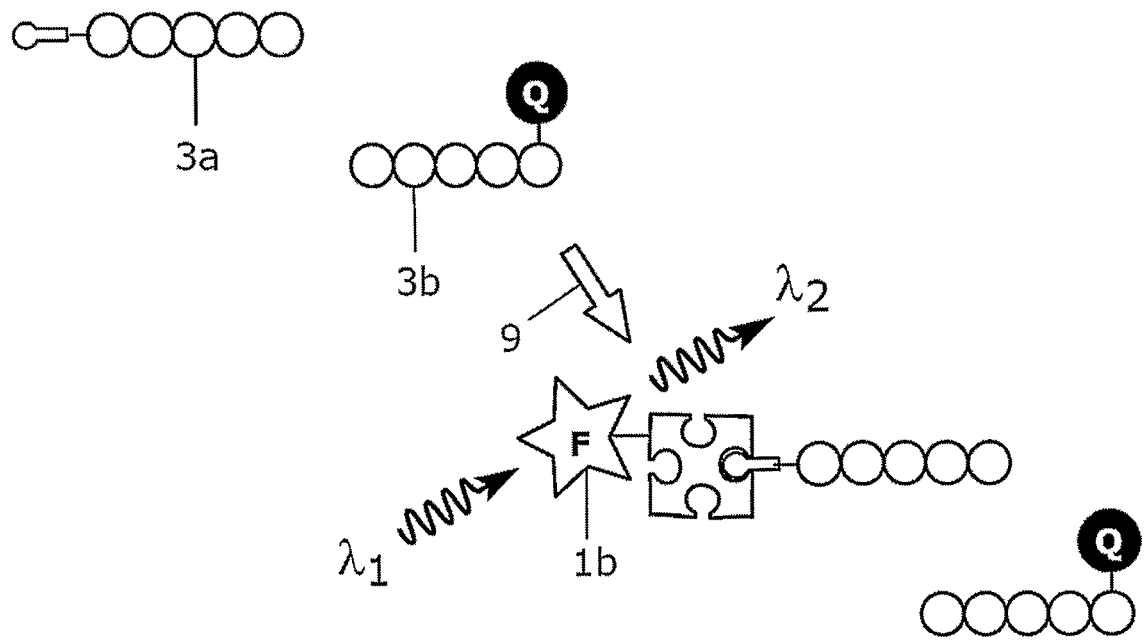

FIG. 2 illustrates the use of a quencher 2 labelled tagged 6 oligomer substrate 3 in combination with a fluorescent compound 1 labelled binder 8 in a cleavage bioassay known from prior art. FIG. 2a shows an intact oligomer substrate 3 containing a tag 6 and labelled with a quencher 2. The intact oligomer 3 has at least one cleavage site 4 where the oligomer 3 can be split to two oligomers or oligomer units. A binder 8 labelled with a fluorescent compound 1 can bind 9 to the tag 6 of the oligomer 3. FIG. 2b shows the same substrate cleaved to two oligomers 3a, 3b. FIG. 2a shows how the tag 6 containing quencher 2 labelled intact oligomer substrate 3 quenches the fluorescence of the fluorescent compound 1a and no fluorescence is produced upon excitation of the fluorescent compound 1a at excitation wavelength $\lambda_1$. In FIG. 2b, however, the fluorescent compound 1b of the binder is fluorescent at emission wavelength $\lambda_2$, because the part 3a of the cleaved substrate not containing the quencher 2 is bound and thus the quencher 2 is not in proximity. The amount of fluorescence at emission wavelength $\lambda_2$ is dependent on cleavage of the intact oligomer substrate 3.

Figure 3A:
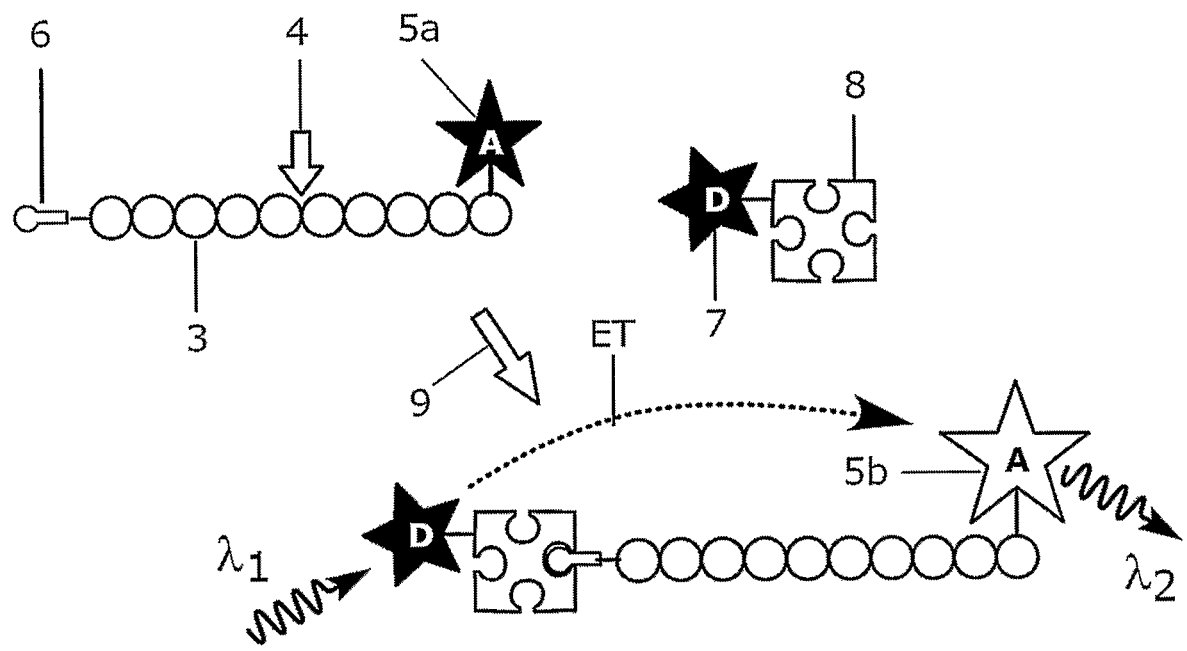
FIG. 3 illustrates the use of acceptor labelled tagged oligomer substrate in combination with donor labelled binder in a further prior art cleavage bioassay.
Figure 3B:
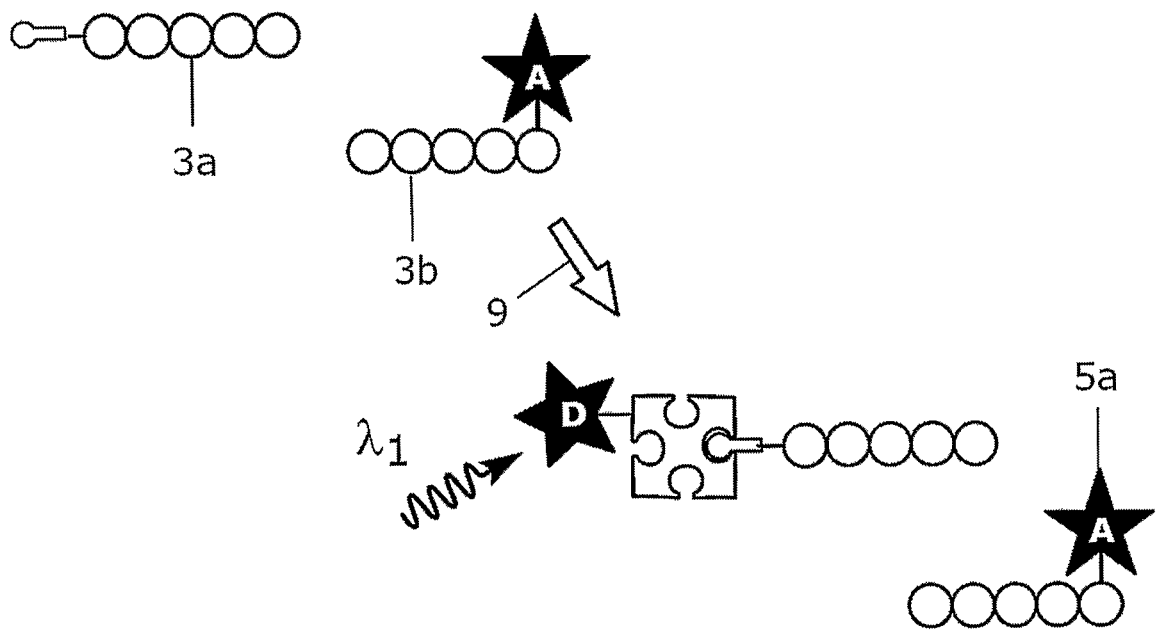

FIG. 3 illustrates the use of a acceptor 5a labelled tagged 6 oligomer substrate 3 in combination with a donor 7 labelled binder 8 in a cleavage bioassay known from prior art. FIG. 3a shows an intact oligomer substrate 3 containing a tag 6 and labelled with an acceptor 5a. The intact oligomer 3 has at least one cleavage site 4 where the oligomer 3 can be split to two oligomers or oligomer units. A binder 8 labelled with a donor 7 can bind 9 to the tag 6 of the oligomer 3. FIG. 3b shows the same substrate cleaved to two oligomers 3a, 3b. FIG. 3a shows how the acceptor label 5b of the tag 6 containing acceptor labelled intact oligomer substrate 3 can receive the excited-state energy of the donor 7 and sensitized emission at emission wavelength $\lambda_2$ is produced upon excitation of the donor 7 at excitation wavelength $\lambda_1$. In FIG. 3*b*, however, the donor 7 of the binder 1*b* is not in proximity of the acceptor 5*a* and no sensitized emission is produced at emission wavelength $\lambda_2$, because the part 3*a* of the cleaved substrate not containing the acceptor is bound. The amount of fluorescence at emission wavelength $\lambda_2$ is inversely dependent on cleavage of the intact oligomer substrate 3.

Figure 4A:
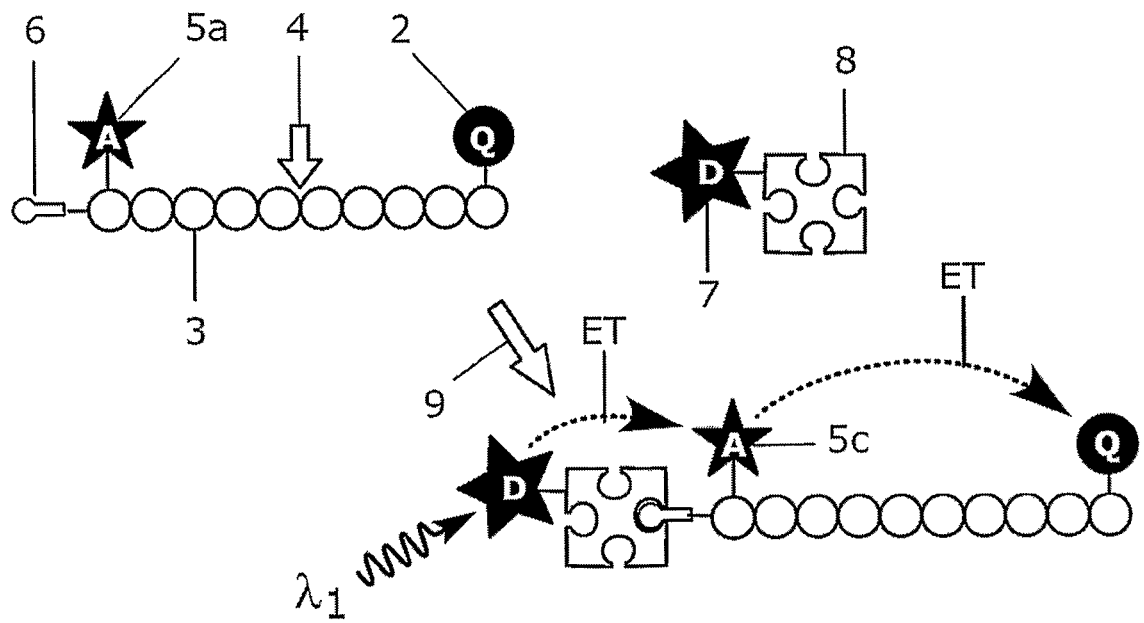
FIG. 4 illustrates the use of dual-labelled tagged oligomer substrate in combination with a donor labelled binder in a cleavage bioassay according to one embodiment of the present invention.
Figure 4B:
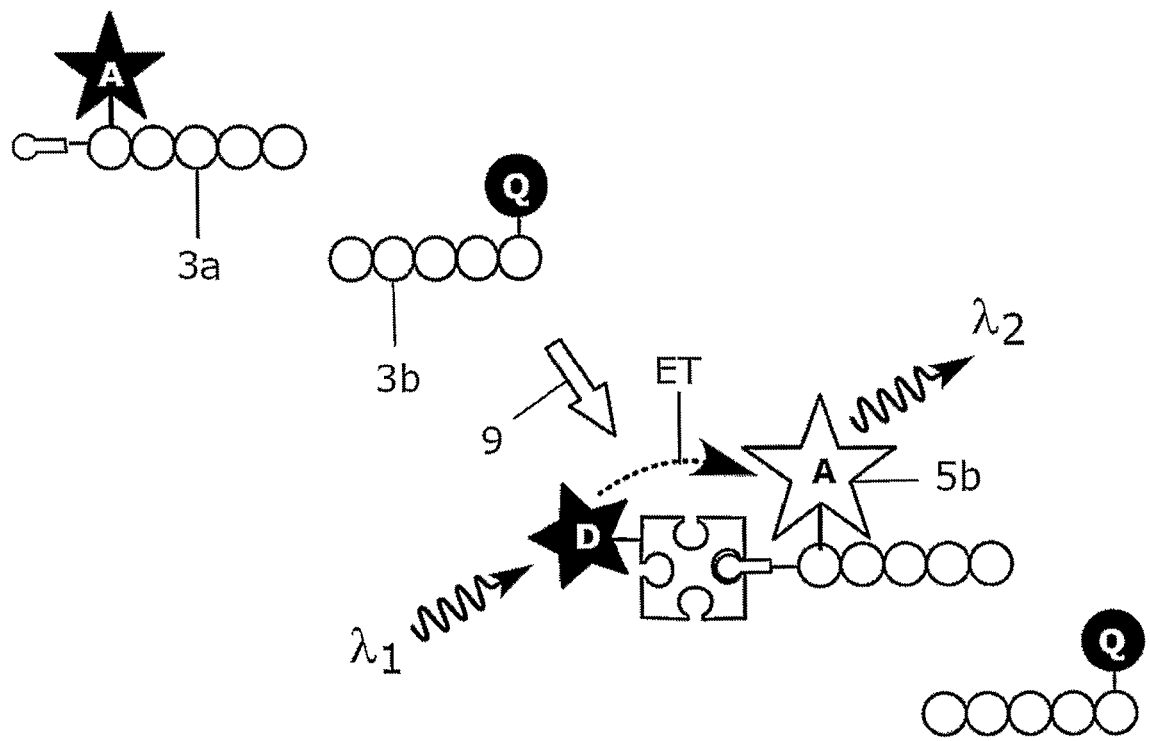

FIG. 4 illustrates the use of a dual-labelled 2, 5*a* tagged 6 oligomer substrate 3 in combination with a donor 7 labelled binder 8 in a cleavage bioassay according to one embodiment of the present invention. FIG. 4*a* shows an intact oligomer substrate 3 containing a tag 6 and labelled with both an acceptor 5*a* and a quencher 2. The intact oligomer 3 has at least one cleavage site 4 where the oligomer 3 can be split to two oligomers or oligomer units. A binder 8 labelled with a donor 7 can bind 9 to the tag 6 of the oligomer 3. FIG. 4*b* shows the same substrate cleaved to two oligomers 3*a*, 3*b*; one oligomer 3*a* containing the tag 6 and the acceptor 5*b*, the other oligomer 3*b* the quencher 2. FIG. 4*a* shows how the intact oligomer substrate 3 containing the tag 6, the acceptor 5*c*, and the quencher 2 labels can receive the excited state energy of the donor 7, but no sensitized emission at emission wavelength $\lambda_2$ is produced upon excitation of the donor 7 at excitation wavelength $\lambda_1$ due to quenching of the fluorescence. In FIG. 4*b*, however, the quencher 2 is not in proximity of the acceptor 5*b* and sensitized emission from the acceptor is produced at emission wavelength $\lambda_2$ upon excitation of the donor, because the part 3*a* of the cleaved substrate containing the acceptor 5*a* and the tag 6 but not the quencher 2 is bound to the binder 8 containing the donor 7. The amount of fluorescence at emission wavelength $\lambda_2$ is dependent on cleavage of the intact oligomer substrate 3.

Figure 5A:
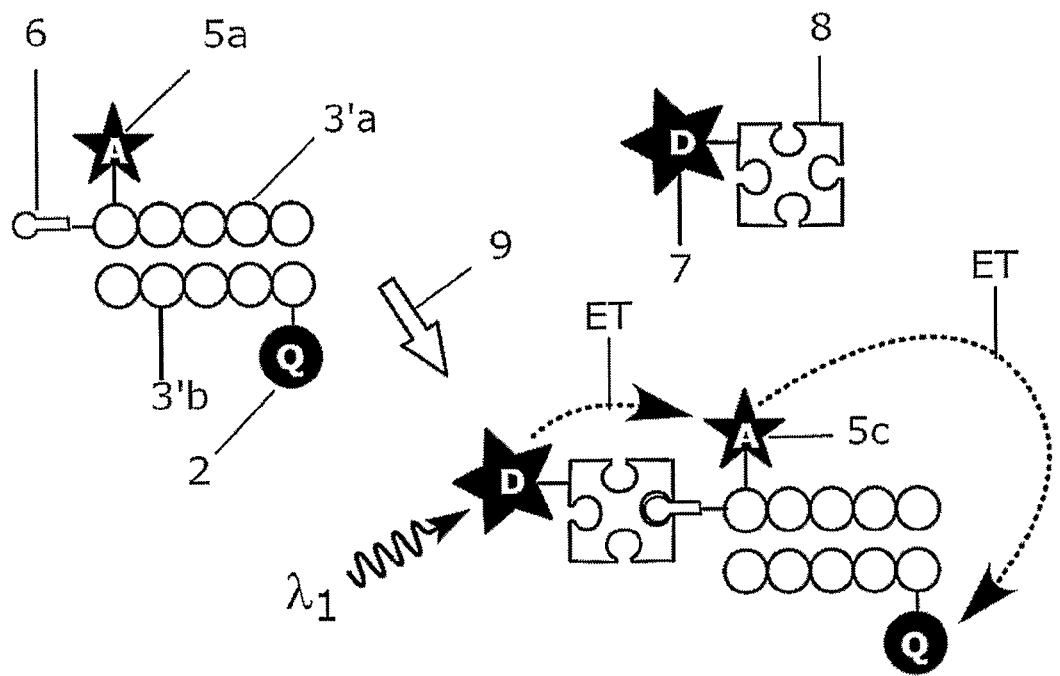
FIG. 5 illustrates the use of both an acceptor-labelled tagged oligomer and a quencher labelled oligomer with a donor labelled binder in a dissociation or association bioassay according to another embodiment of the present invention.
Figure 5B:
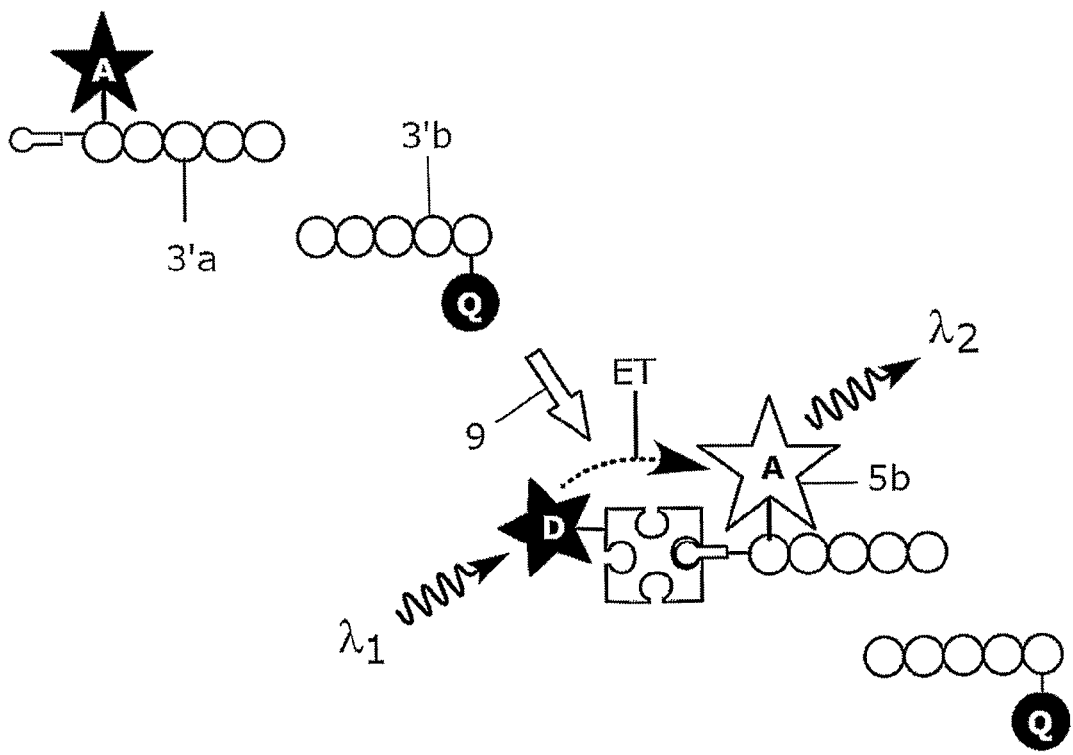

FIG. 5 illustrates the use of both a acceptor-labelled 5*a* tagged 6 oligomer 3'*a* and a quencher 2 labelled oligomer 3'*b* with a donor 7 labelled binder 8 in a dissociation or association bioassay according to another embodiment of the present invention. FIG. 5*a* shows two oligomers 3'*a*, 3'*b* associated to each other reversibly; one oligomer 3'*a* contains a tag 6 and is labelled with acceptor 5*a*, the other oligomer 3'*b* is labelled with a quencher 2. A binder 8 labelled with a donor 7 can bind 9 to the tag 6 of one of the oligomers 3'*a*. FIG. 5*b* shows the two oligomers 3'*a*, 3'*b* dissociated. FIG. 5*a* shows how the acceptor label 5*c* of the oligomer 3'*a* containing both the tag 6 and the acceptor 5*a* can receive the excited-state energy of the donor 7, but when the other oligomer 3'*b* labelled with the quencher 2 is associated no sensitized emission at emission wavelength $\lambda_2$ is produced upon excitation of the donor 7 at excitation wavelength $\lambda_1$ due to quenching of the fluorescence In FIG. 5*b*, however, the oligomers 3'*a*, 3'*b* are dissociated and sensitized emission is produced at emission wavelength $\lambda_2$, because the quencher 2 is not in proximity of the acceptor 5*b*. The amount of fluorescence at emission wavelength $\lambda_2$ is dependent on the concentration of the dissociated form of the oligomer 3'*a* containing the tag 6 and labelled with the acceptor 5*b*.

Figure 6A:
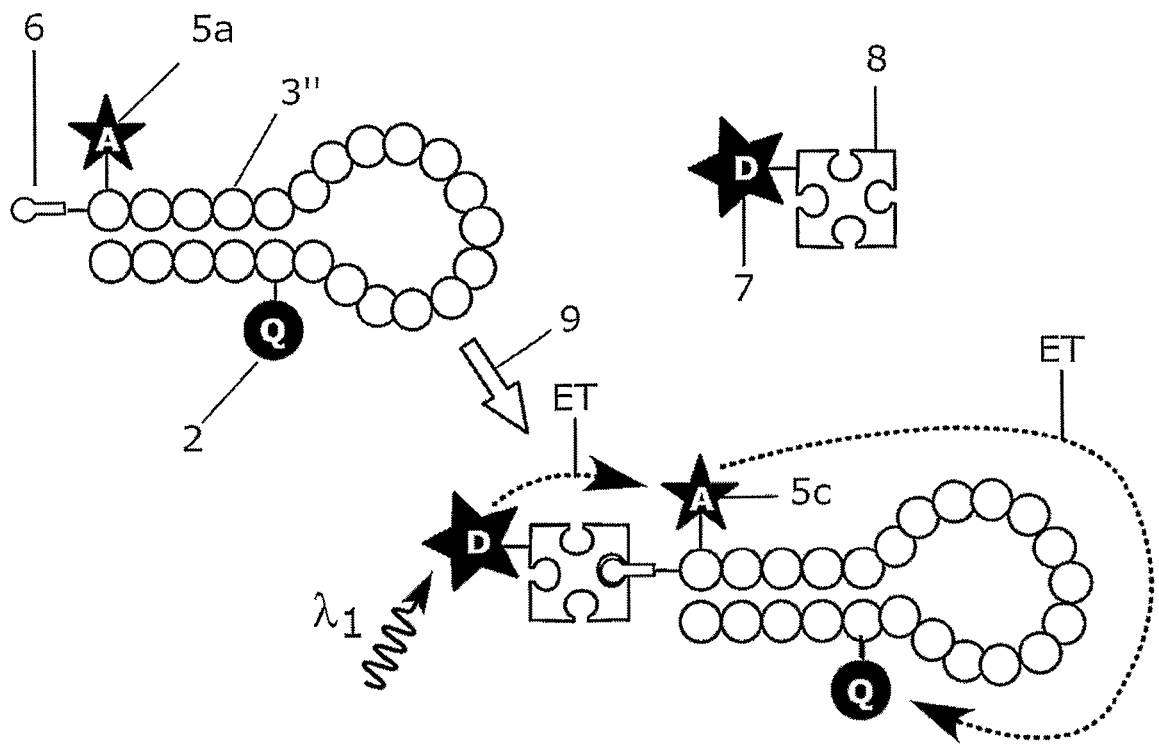
FIG. 6 illustrates the use of a dual-labelled tagged oligomer with a donor labelled binder in a conformation change bioassay according to a further embodiment of the present invention.
Figure 6B:
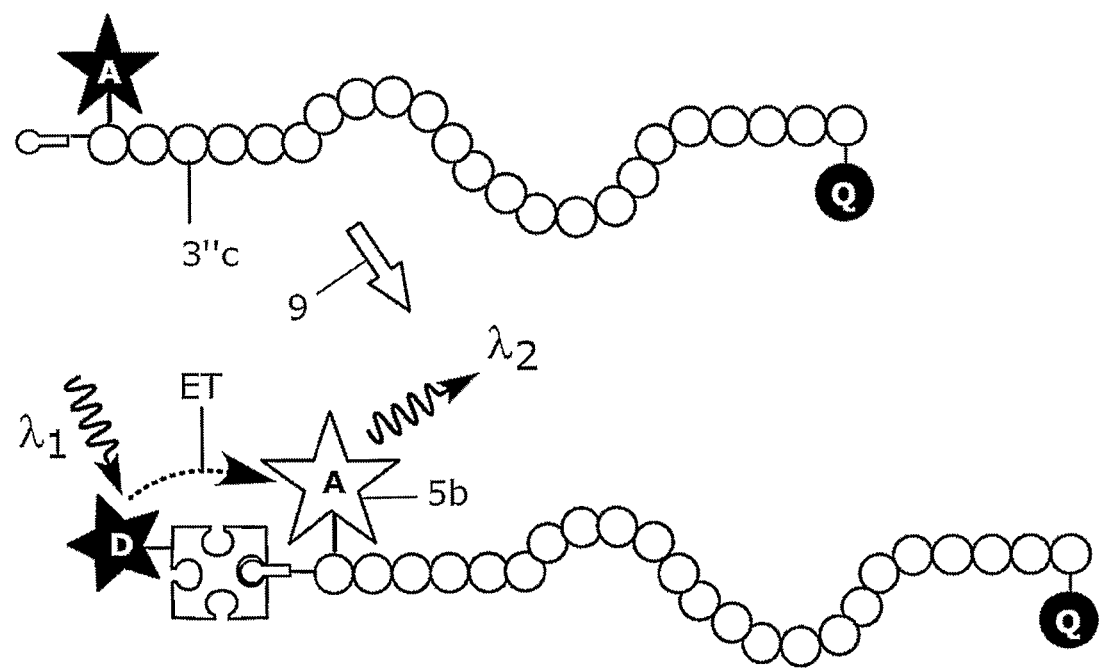

FIG. 6 illustrates the use of a dual-labelled 2, 5*a* tagged 6 oligomer 3" and with donor 7 labelled binder 8 in a conformation change bioassay according to yet another embodiment of the present invention. FIG. 6*a* shows an oligomer 3" containing a tag 6 and labelled with both an acceptor 5*a* and a quencher 2 in a closed conformation. A binder 8 labelled with a donor 7 can bind 9 to the tag 6 of the oligomer. FIG. 6*b* shows the same substrate in open conformation 3"*c*, where the distance between the acceptor 5*a* the quencher 2 is increased. FIG. 6*a* shows how the acceptor label 5*c* of the oligomer substrate 3" containing the tag 6, the acceptor 5*a* and the quencher 2 label can receive the excited state energy of the donor 7, but no sensitized emission at emission wavelength $\lambda_2$ is produced upon excitation of the donor 7 at excitation wavelength $\lambda_1$. In FIG. 6*b*, however, the quencher 2 is not in close proximity of the acceptor 5*b* and sensitized emission is produced at emission wavelength $\lambda_2$, because the substrate is in open conformation 3"*c*. The amount of fluorescence at emission wavelength $\lambda_2$ is dependent on the amount of the oligomer in open conformation 3"*c*.

FIG. 7 illustrates measurement of biotin Cy5 dye conjugate based on the intrinsic short-lifetime fluorescence of the Cy5 dye. The squares represent the measured signals and the dashed line illustrates the limit of detection calculated as background plus three times standard deviation.

FIG. 8 illustrates measurement of the cleavage of the biotin-Cy5-oligo-BHQ2 conjugate based on the intrinsic short-lifetime fluorescence of the Cy5 dye (squares) and based on the sensitized acceptor emission of Cy5 upon excitation of the europium(III) chelate-dyed nanoparticle donor (triangles). The plotted symbols indicate the difference between signals of the reaction containing the enzyme and the control without enzyme for each oligonucleotide substrate concentration. The dashed lines illustrate the limits of detection calculated as background plus three times standard deviation for both measurements.

FIG. 9 illustrates measurement of the cleavage of the biotin-Cy5-oligo-BHQ2 conjugate based on the intrinsic short-lifetime fluorescence of the Cy5 dye (squares) and based on the sensitized acceptor emission of Cy5 upon excitation of the europium(III) chelate (circles). The plotted symbols indicate the difference between signals of the reaction containing the enzyme and the control without enzyme for each oligonucleotide substrate concentration. The dashed lines illustrate the limits of detection calculated as background plus three times standard deviation for both measurements.

Preferred Donor Labels

Preferred luminescent donor labels of some embodiments of the invention are selected from the group consisting of long-lifetime luminescence labels (fluorescence lifetime over 1 µs), up-converting luminescence labels (excitation at longer wavelength than emission) and electrogenerated luminescence labels (excited by electric voltage or current).

Employment of a long-lifetime particulate donor with a short lifetime fluorescent acceptor in ligand binding assays is described in WO 02/44725 and in WO 2004/096944, containing description of preferred particulate long-lifetime fluorescent donor labels. Time-resolved homogeneous fluorometric assays and a list of preferred small molecule lanthanide labels comprising both cryptates and chelates have been described in U.S. Pat. No. 5,998,146, Mathis G, Probing molecular interactions with homogeneous techniques based on rare earth cryptates and fluorescence energy transfer, *Clin Chem*. 1995; 41: 1391-1397 and WO 98/015830. Preferred long-lifetime fluorescent porphyrin labels have been described in O'Riordan T. C., Ponomarev G. V. Yashunsky D. V., Papkovsky D. B. Homogeneous assays for cellular proteases employing the platinum(II)-coproporphyrin label and time-resolved phosphorescence, Analytical Biochemistry 2005; 342: 111-119 and Burke M., O'Sullivan P., Soini A., Berney H., Papkovsky D. B. Evaluation of the phosphorescent palladium(II)-coproporphyrin labels in separation-free hybridisation assays, *Anal Biochem* 2003; 320, 273-280.

Preferred up-converting lanthanide labels and their applications have been described in Corstjens P et al., *Clin Chem* 2001; 47:1885-1893; Niedbala R S et al., *Anal Biochem* 2001; 293:22-30; van De Rijke F et al., Nat Biotechnol 2001; 19:273-276; and Zijimans HJMAA et al., *Anal Biochem* 1999; 267:30-36, and in addition in WO 94/07142, U.S. Pat. Nos. 5,674,698, 6,159,686 and 6,312,914. WO 02/44725 also covers the use of long-lifetime fluorescent anti-Stokes phosphors as donors in combination with short-lifetime fluorescent acceptor. The homogeneous assay principle based on up-converting phosphors has been described in WO 98/43072 and in more detail in US 2002/0119485 and Kuningas K et al. Homogeneous Assay Technology Based on Upconverting Phosphors *Anal. Chem.* 2005; 77: 7348-7355. WO 2004/086049 describes the use of anti-Stokes phosphors in homogeneous fluorescence resonance energy transfer assays in whole blood. Up-converting chelates have been described in U.S. Pat. No. 5,891,656 and Faris G W and Hryndza M, *Proc SPIE—Int Soc Opt Eng* 2002; 4626: 449-452. Excitation of up-converting labels can be performed with e.g. pulsed halogen lamps or semiconductor light-emitting diodes or lasers, which are compact, have high power and are also inexpensive (Johnson B D, *Photonics Spectra* 2001; 35: 52). The exciting radiation employed in the up-conversion is not sufficiently energetic to excite background from the sample or surroundings with multi-photon excitation at a wavelength, which would interfere with the measurement.

Preferred electrogenerated luminescence and electrochemiluminescence donor labels have been described by Kulmala S. and Suomi J. Current status of modern analytical luminescence methods *Analytica Chimica Acta*, 2003; 500: 21-69 and Kulmala S., Ala-Kieme T., Latva M., Loikas K., and Takalo H. Hot Electron-Induced Electrogenerated Chemiluminescence of Rare Earth(III) Chelates at Oxide-Covered Aluminum Electrodes. *J. Fluor.* 1998; 8: 59-65. Hot electron-induced excitation of lanthanide chelates, such as phenolic terbium chelates, enables long-lifetime luminescence and improved limit of detection.

The preferred donor compounds can also be embedded in a solid-surface or a surface coating. Biomolecules can be attached to the solid-surface or to the surface coating. Example of a surface coating containing organo-metallic complexes which can participate in energy transfer has been described in US 2002/0076830.

Preferred Binders and Tags

Preferred pairs of binder and tag forming suitable strong binding interaction to be employed in the present invention are, but not limited to, streptavidin and biotin, avidin and biotin, oligonucleotide and oligonucleotide, antibody and peptide, antibody and fluorescein, antibody and acceptor dye, protein and peptide, and protein and oligonucleotide. Biotin and other tags can be their derivatives containing different spacer arm for conjugation to other molecules. Antibodies can be also antibody fragments, e.g. scFv or Fab fragments generated either enzymatically or using recombinant DNA.

Preferred Acceptor and Quencher Labels

A luminescent acceptor label is preferably excited by absorption of light at the wavelength of major or significant emission of a donor label, and it preferably emits at a wavelength of none or minimal emission intensity of a donor label. Criteria for selection are described e.g. in WO 98/15830 and U.S. Pat. No. 5,998,146. Overlapping of the donor emission spectra and the excitation spectra of the acceptor is not an unconditional requirement. Especially, when luminescent lanthanides are employed as donors the fluorescence resonance energy transfer does not necessarily follow Förster definitions (Laitala V, Hemmila I. Homogeneous assay based on anti-stokes' shift time-resolved fluorescence resonance energy-transfer measurement. *Anal Chem* 2005; 77: 1483-1487; and US 2005/0123957).

Energy from a donor label can be transferred to one or more acceptor labels of the same or different types of acceptor labels. A luminescent acceptor label can be a single luminescent molecule or combination of different luminescent molecules selected to allow increased Stokes' shift as described in patent U.S. Pat. No. 6,673,943. The preferred luminescent acceptor label is selected from the group consisting of rapidly decaying, short-lifetime fluorophores (fluorescence lifetime below 1 μs). The luminescent acceptor label or a part of it can also be a near-infrared fluorescent protein (Trinquet E et al. *Anal Biochem* 2001; 296:232-244; Kronick M N, J *Immunol Methods* 1986; 92:1-13; Fradkov A F, et al., *FEBS Lett* 2000; 479:127-130).

Especially suitable acceptor fluorophores are e.g. fluorescent phycobiliproteins available from Cyanotech Corporation (www.phycobiliprotein.com), Alexa Fluor and BODIPY series available from Molecular Probes (www.probes.com), Cy-dyes from Amersham Biosciences (www.amershambiosciences.com), EVOblue and DY-dyes from Dyomics (ww.dyomics.com), Atto-Dyes from Atto-tec (www.atto-tec.de) and Oyster-dyes from Denovo Biolabels (www.biolabel.de). Dimeric fluorescent energy transfer dyes, tandem dyes and energy-transfer cassettes, comprising two fluorescent molecules are preferred for their property of large and tunable Stokes' shift (U.S. Pat. No. 5,565,554; WO9939203; EP 0747700 A2; Burghart, A et al., *Chem Commun* 2000; 22: 2203-2204) enable utilization of optimal excitation and emission wavelengths.

Selection of acceptors for up-converting lanthanide donor is described in WO 2004/086049 and for long-lifetime lanthanide donor in U.S. Pat. No. 5,998,146 and WO 98/015830. The preferable acceptor label should be selected to have an excitation spectrum with overlaps at least partially with peaks of the emission spectrum of the donor label and has an emission maximum at wavelength where the emission of the donor is at minimal level.

As specific examples can be mentioned allophycocyanin, Cy 3, Alexa 547, Alexa 555, Cy 5, Cy 5.5, Alexa 647 and Alexa 680, which are suitable to be used as acceptor labels together with described long-lifetime lanthanide donor labels, and B-phycoerythrin, R-phycoerythrin, Alexa 546, Alexa 555, Alexa 660, Alexa 680 and Alexa 700, which are suitable to be used as acceptor labels together with described up-converting lanthanide labels as donor labels.

A non-luminescent quencher label can be a single molecule (U.S. Pat. No. 6,329,205B1), gold cluster (Dubertret B, Calame M, and Libchaber A J, *Nat Biotechnol.* 2001; 19: 365-70) or nanoparticle dyed with light absorbing molecules. Selection of quencher labels is explained in U.S. Pat. No. 5,998,146 and US 2005/0123957. Especially suitable acceptor fluorophores are e.g DABCYL and QSY-series from Molecular Probes (www.probes.com), Dark Cy-dyes from Amersham Biosciences (www.amershambiosciences.com), Eclipse™ Dark Quencher-dyes from Epoch Biosciences (www.epochbio.com), Black Hole Quencher dyes from Biosearch Technologies (www.biosearchtech.com), DYQ-dyes from Dyomics (www.dyomics.com), Black Berry Quenchers from Berry&Associates (www.berryassoc.com), and Elle- Quencher from Oswel (www.oswel.com). As specific examples can be mentioned QSY-21 and Black Hole Quencher 3, which are suitable to be used as quencher labels together with described preferred acceptor labels and up-converting or long-lifetime lanthanide donors. Both quencher dyes have strong absorption at 600-700 nm and have no luminescence emission.

Other Preferred Embodiments

FIG. 4 shows one embodiment of the present invention, where a biotinylated quenched fluorescent substrate (comprising of a first and a second group bound covalently) can be cleaved enzymatically (to separate the two groups). The donor labelled streptavidin (a third group) is added and the sensitized emission is measured upon excitation of the donor. Only the signal of the cleaved substrate (FIG. 4b) is measurable while the intact substrate (FIG. 4a) does not fluoresce upon excitation of the donor. The measured signal is increased with increased enzymatic activity.

FIG. 5 shows another embodiment of the present invention, where two components of the binding pair, one component labelled with biotin and acceptor (a first group) and the other with quencher (a second group), can bind reversible with each other. Binding of the two binding pairs can be decreased or increased upon addition of a modulating compounds, e.g. decreased upon addition of a compound capable to bind to either of the two components of the binding pair and thus competing with the other of the two components. The donor labelled streptavidin (a third group) is added and the sensitized emission is measured upon excitation of the donor. Only the signal of the dissociated binding pair (FIG. 5b) is measurable while the associated binding pair (FIG. 5a) does not fluoresce upon excitation of the donor. The measured signal is increased with e.g. increased concentration with the competing compound.

FIG. 6 shows yet another embodiment of the present invention, where the conformation of a biotinylated quenched fluorescent oligomer (comprising of a first and a second group bound covalently) can be changed (to change distance between the two groups); e.g. the structure of a molecular beacon type oligonucleotide can be changed due to increase in temperature or addition of an oligonucleotide containing a complementary sequence. The donor labelled streptavidin (a third group) is added and the sensitized emission is measured upon excitation of the donor. Only the signal of the opened conformation (FIG. 6b) is measurable while the closed conformation (FIG. 6a) does not fluoresce upon excitation of the donor. The measured signal is increased with e.g. increased concentration of the complementary nucleotide sequence.

The bioassay according to this invention can be either a non-competitive assay or a competitive assay.

The bioassay according to the present invention is preferred to be carried out in two incubation steps, the second incubation step being the binding reaction of the binder of the third group to the tag of the first group after addition of the third group.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive

EXAMPLES

Example 1

A minoreactive CyDye Fluor Cy 5 obtained from Amersham Biosciences (Uppsala, Sweden) was conjugated to an aminoderivative of biotin (2-(((N-(biotinoyl)amino)hexanoyl)amino)ethylamine; Molecular Probes, Leiden, Netherlands) to produce a biotinylated conjugate of Cy 5 dye. The conjugation reaction contained 0.1 mg of Cy 5 dissolved in 50 mmol/l carbonate buffer, pH 9.3 with 20% (v/v) dry DMF and a 20-fold molar excess of aminoderivative biotin in total volume of 100 µl. The reaction was incubated at +35° C. for 3 h and purified with HPLC using a C18-RP-column (JonesChromatography, Mid Glamorgan, UK). The biotinylated conjugate of the Cy 5 dye was diluted in water to concentrations of 0.1 nmol/l to 500 nmol/l. Fluorescence of the dye was measured from a 200 µl volume of each dilution and blank from clear 96-well microtitration plate wells using fluorescence mode of Wallac Victor multilabel counter with an excitation filter at 615 nm and emission filter at 665 nm. The results are shown in FIG. 7 indicating a detection limit (background+3× standard deviation) of the dye conjugate of approximately 1.5 nmol/l.

Example 2

Synthetic oligonucleotide substrate 5'-TC TGA GGG TGA ACT TGC G-3', labelled from 5' end with a dual function building block containing both biotin and Cy 5 and from 3' end with BHQ-2, was obtained from Thermo Electron Corporation.

The complete sequence of the oligonucleotide substrate is
biotin-Cy 5-5' TC TGA GGG TGA ACT TGC G 3'-BHQ-2
wherein
Cy 5=CyDye Fluor Cy 5 from Amersham Biosciences
BHQ-2=Black Hole Quencher 2 from Biosearch Technologies and its molecular weight is 7071.1 g/mol.

Europium(III)-chelate dyed Fluoromax nanoparticles 92 nm in diameter, obtained from Seradyn Inc (Indianapolis, Ind.), were coated with streptavidin according to Härmä, H., et al. Europium nanoparticles and time-resolved fluorescence for ultrasensitive detection of prostate-specific antigen in *Clin Chem* 2001; 47: 561-568. Nanoparticles were prewashed with 10 mmol/l phosphate buffer, pH 7.0, on a Nanosep microporous centrifugal filter (300 kDa cutoff; Pall Filtron, Northborough, Mass.). Phosphate buffer was added to the particles, and the solution was sonicated with a tip sonicator (Labsonic U; B. Braun, Leverkusen, Germany) at 80 W for 5 s. Carboxyl groups on the surface of nanoparticles were activated with 10 mmol/l N-(3-dimethylaminopropyl)-N9-ethyl-carbodiimide and N-hydroxysulfosuccinimide (Fluka, Buchs, Switzerland) for 30 min. The activated particles were washed once with 10 mmol/l carbonate buffer, pH 9.0, and 15 µmol/l streptavidin was added. After 2 h of incubation, the streptavidin-coated particles were washed five times with a 2 mmol/l Tris-HCl solution, pH 7.0, and stored at 4° C.

The oligonucleotide substrate was diluted to concentrations of 0.01-10 nmol/l in 50 mmol/l Tris-HCl, pH 8.0, containing 0.1% BSA (bovine serum albumin) and 1 mmol/l $MgCl_2$. Thereafter, a 20 µl aliquot of each substrate dilution and blank was added to clear 96-well microtitration plate wells saturated previously with BSA. In addition, 0.5 Units of Benzonase (Purity Grade II; obtained from Merck, Darmstadt, Germany) was added in a 5 µl volume to each well. Control reactions containing the oligonucleotide substrate but no enzyme where prepared by adding 0 (zero) Units of Benzonase The digestion reactions were incubated for 30 min at 37° C. with slow shaking and fluorescence of Cy5 dye was measured as in example 1.

To improve the detection according to the present invention, $5 \cdot 10^7$ streptavidin-coated europium chelate-dyed nanoparticles were added to each well in a 25 µl volume of assay buffer (50 mmol/l Tris-HCl, pH 7.75, containing 0.9% (w/v) NaCl, 0.05% (w/v) NaN$_3$, 0.01% (v/v) Tween40, 0.05% (w/v) bovine-γ-globulin, 20 µmol/l diethylenetriamine-pentaacetate (DTPA) and 0.5% (w/v) BSA). The reactions were incubated for additional 30 min at room temperature with shaking to allow biotinylated substrates to bind to streptavidin-coated nanoparticles and Cy5 fluorescence was measured thereafter in time-resolved mode by Wallac Victor multilabel counter with an excitation filter at 340 nm, an emission filter at 665 nm, 1000 cycles, delay 75 µs and a window 400 µs. Results are shown in FIG. 8 indicating a detection limit of 0.07 nmol/l for the described assay based on a europium chelate-dyed nanoparticle donor.

Example 3

Streptavidin was labelled with fluorescent europium chelate labelling reagent {2,2',2'',2'''-{[2-(4-isothiocyanatophenyl)ethylimino]bis(methylene)bis{4-{[4-(α-galactopyranoxy)phenyl]ethynyl}pyridine-6,2-diyl}bis (methylenenitrilo)}tetrakis(acetato)}europium(III) (von Lode P, Rosenberg J, Pettersson K, and Takalo H. A europium chelate for quantitative point-of-care immunoassays using direct surface measurement; *Anal Chem* 2003; 75: 3193-201). The labelling of streptavidin performed in 50 mmol/l sodium carbonate buffer, pH 9.8, using 50-fold molar excesses of the chelate labelling reagent. The reaction was carried out overnight at room temperature and the excess free labelling reagent removed on NAP-5 and NAP-10 (Amersham Biosciences) chromatography columns using Tris-saline-azide (6.1 g/l Tris, 9.0 g/l NaCl, and 0.5 g/l NaN$_3$), pH 7.75, as elution buffer. The fractions containing the streptavidin was collected and the europium concentrations were measured against a europium calibrator using DELFIA method (Wallac Oy; Perkinelmer Life and Analytical Sciences, Turku, Finland). The labelling degrees obtained was 4.2 Eu/SA. Finally, bovine serum albumin was added to a concentration of 1 g/l to the solution containing the europium-labelled streptavidin. The labelled streptavidin were stored at 4° C.

Otherwise, the experiment was carried out equally to experiment 2 until 0.5 µmol of fluorescent europium chelate-labelled streptavidin was added to each well in a 25 µl volume of assay buffer instead of addition of $5 \cdot 10^7$ streptavidin-coated europium chelate-dyed nanoparticles. The final concentration of the fluorescent europium chelate-labelled streptavidin was 10 nmol/l. The reactions were incubated for additional 30 min at room temperature with shaking to allow biotinylated substrates to bind to labelled streptavidin and the Cy5 fluorescence was measured thereafter in time-resolved mode by Wallac Victor multilabel counter with excitation filter at 340 nm, emission filter at 665 nm, 1000 cycles, delay 75 µs and window 400 µs. Results are shown in FIG. 9 indicating a detection limit 0.25 nmol/l for the described assay based on a intrinsically fluorescent lanthanide chelate donor.

---

---

The invention claimed is:

1. A homogenous assay method for measurement of biological activity, its modulation or analyte concentration of a sample, comprising
 a) bringing a sample, a first group, a second group and optionally a third group, in contact with each other to obtain an assay mixture,
 b) allowing the assay mixture to react,
 c) bringing the third group in contact with the assay mixture if it was not brought in contact with the assay mixture in step a),
 d) allowing the third group to react with the assay mixture if it was brought in contact with the assay mixture in step c),
 e) exciting a donor, and
 f) measuring a sensitized emission of an acceptor,
wherein
 i) said first group comprises an acceptor, which acceptor is a short lifetime fluorescent compound capable of energy transfer, and
 ii) said second group comprises a quencher, which quencher is capable of energy transfer from an acceptor, and
 iii) said third group comprises a donor for energy transfer to said acceptor, which donor is an up-conversion fluorescent compound, a long-lifetime fluorescent compound or an electrogenerated luminescent compound; and said first group comprises a tag, said third group comprises a binder, and said binder has a high affinity for binding to said tag; and said sensitized emission of said acceptor is fluorescence brought about by exciting the donor resulting in energy being transferred from the donor to the acceptor, such that the increase or decrease, respectively, of fluorescence of said acceptor due to the decrease or increase, respectively, of energy transfer from said acceptor to said quencher resulting from lengthening or shortening, respectively, of the distance between said acceptor and quencher is measured.

2. The assay method according to claim 1 wherein the quencher is non-luminescent.

3. The assay method according to claim 1 wherein the donor is excited either by light or electrochemically.

4. The assay method according to claim 1 wherein the first group and the second group are covalently linked, by a covalent linkage, and lengthening of the distance between the acceptor and quencher results from cleavage of the first group from the second group by cleavage of the covalent linkage.

5. The assay method according to claim 4 wherein the first group and/or the second group comprises an oligopeptide, oligonucleotide or oligosaccharide.

6. The assay method according to claim 4 wherein cleavage of the first group from the second group is enzymatic.

7. The assay method according to claim 1 wherein the first group and the second group are covalently linked and the covalently linked first and second group comprises different tertiary structures or conformations, and the shortening or lengthening of the distance between the acceptor and quencher results from a change in tertiary structure or conformation.

8. The assay method according to claim 7 wherein the first group and/or the second group comprises an oligopeptide, oligonucleotide or oligosaccharide.

9. The assay method according to claim 1 wherein the first group and the second group have an affinity towards each other and the shortening or lengthening, respectively, of the distance between the acceptor and quencher results from association or dissociation, respectively, of said first and second groups.

10. The assay method according to claim 9 wherein the first group and the second group each comprise an oligonucleotide.

11. The assay method according to claim 1, wherein the third group is brought in contact with the assay mixture in step c) and allowed to react with the assay mixture in step d).

12. The assay method according to claim 1, wherein the third group is a particulate comprising one or more donors and one or more binders.

13. The assay method according to claim 12 wherein the particulate has a diameter of <10 µm.

14. The assay method according to claim 1 wherein the third group is incorporated in a solid-surface or a surface coating comprising one or more donors and one or more binders.

15. A kit for a homogenous bioassay according to claim 1 wherein said kit comprises reagents including
   i) a first group comprising an acceptor, which acceptor is a short lifetime fluorescent compound capable of energy transfer, and
   ii) a second group comprising a quencher, which quencher is capable of energy transfer from an acceptor, and
   iii) a third group comprising a donor for energy transfer to said acceptor, which donor is an up-conversion fluorescent compound, a long-lifetime fluorescent compound or an electrogenerated luminescent compound; and
said first group comprises a tag, said third group comprises a binder, and said binder has a high affinity for binding to said tag.

16. The kit according to claim 15 wherein the quencher is non-luminescent.

17. The kit according to claim 15 wherein the first group and the second group are covalently linked, by a covalent linkage.

18. The kit according to claim 17, wherein the covalently linked first and second group comprises different tertiary structures or conformations.

19. The kit according to claim 15 wherein the first group and/or the second groups comprises an oligopeptide, oligonucleotide or oligosaccharide.

20. The kit according to claim 15 wherein the first group and the second group have an affinity towards each other.

21. The kit according to claim 15 wherein the third group is a particulate comprising one ore more donors and one or more binders.

22. The kit according to claim 21 wherein the particulate has a diameter of <10 µm.

23. The kit according to claim 15 wherein the third group is incorporated in a solid-surface or a surface coating comprising one or more donors and one or more binders.

* * * * *

SEQUENCE LISTING

<160> NUMBER OF SEQ ID NOS: 1

<210> SEQ ID NO 1
<211> LENGTH: 18
<212> TYPE: DNA
<213> ORGANISM: Artificial Sequence
<220> FEATURE:
<223> OTHER INFORMATION: Oligonucleotide Substrate

<400> SEQUENCE: 1
tctgagggtg aacttgcg                                           18